(12) United States Patent
Lee et al.

(10) Patent No.: US 12,330,127 B2
(45) Date of Patent: *Jun. 17, 2025

(54) AQUEOUS SYSTEMS OF AT LEAST TWO PHASES CONTAINING MICROCAPSULES AND PROCESSES FOR MANUFACTURING THE SAME

(71) Applicant: The Trustees of the University of Pennsylvania, Philadelphia, PA (US)

(72) Inventors: Daeyeon Lee, Wynnewood, PA (US); Kathleen J Stebe, Penn Valley, PA (US); Sarah D Hann, Yardley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/537,840

(22) Filed: Nov. 30, 2021

(65) Prior Publication Data

US 2022/0088556 A1 Mar. 24, 2022

Related U.S. Application Data

(63) Continuation of application No. 15/952,321, filed on Apr. 13, 2018, now Pat. No. 11,260,358.

(Continued)

(51) Int. Cl.
*B01J 13/10* (2006.01)
*A61K 9/50* (2006.01)
(Continued)

(52) U.S. Cl.
CPC ............. *B01J 13/10* (2013.01); *A61K 9/5031* (2013.01); *A61K 9/5036* (2013.01); *A61K 35/74* (2013.01);

(Continued)

(58) Field of Classification Search
None
See application file for complete search history.

(56) References Cited

U.S. PATENT DOCUMENTS 6,861,064 B1 * 3/2005 Laakso .................... B01J 13/18
427/213.3
11,260,358 B2 * 3/2022 Lee ......................... A61K 35/74

OTHER PUBLICATIONS

Fukui et al., Colloids Surf. A, 2010, 370(1-3), pp. 28-34. (Year: 2010).*

(Continued)

*Primary Examiner* — Brian Gulledge
(74) *Attorney, Agent, or Firm* — BakerHostetler

(57) ABSTRACT

In one aspect of the invention, a microcapsule includes a film encapsulating a material. The film is formed by complexation of at least two mutually attractive components initially present in an aqueous dispersion comprising a continuous phase and a dispersed phase. The at least one first component is initially present in the continuous phase and the at least one second component is initially present in the dispersed phase. According to another aspect of the invention, provided is a process for forming microcapsules including the step of injecting a dispersed phase having at least a first component into a continuous phase having at least a second component, where the first component and the second component are mutually attractive, such that a film is formed by complexation of the first charged component and the second charged component.

7 Claims, 30 Drawing Sheets

Related U.S. Application Data

(60) Provisional application No. 62/486,154, filed on Apr. 17, 2017.

(51) Int. Cl.

| | | |
|---|---|---|
| *A61K 35/74* | (2015.01) | |
| *B01J 13/04* | (2006.01) | |
| *C12N 11/04* | (2006.01) | |
| *C12N 11/082* | (2020.01) | |
| *C12N 11/087* | (2020.01) | |
| *C12N 11/089* | (2020.01) | |
| *C12N 11/098* | (2020.01) | |
| *C12N 11/10* | (2006.01) | |
| *A61K 35/12* | (2015.01) | |

(52) U.S. Cl.
CPC ............... *B01J 13/04* (2013.01); *C12N 11/04* (2013.01); *C12N 11/082* (2020.01); *C12N 11/087* (2020.01); *C12N 11/089* (2020.01); *C12N 11/098* (2020.01); *C12N 11/10* (2013.01); *A61K 2035/128* (2013.01)

(56) References Cited

OTHER PUBLICATIONS

U.S. Appl. No. 15/952,321, filed Apr. 13, 2018.
Antipov et al., "Polyelectrolyte Multilayer Capsule Permeability Control", Colloids and Surfaces A: Physiochemical and Engineering Aspects, Feb. 18, 2002, vols. 198-200, pp. 535-541 (Abstract Only).
Antipov et al., "Polyelectrolyte Multilayer Capsules as Vehicles with Tunable Permeability", Advances in Colloid and Interface Science, 2004, vol. 111, pp. 49-61.
Atefi et al., "Unlralow Interfacial Tensions of Aqueous Two-Phase Systems Measured Using Drop Shape", Langmuir, 2014, vol. 30, pp. 9691-9699.
De Graff, "Texture and Satiation: The Role of Oro-Sensory Exposure Time", Physiology & Behavior, 2012, vol. 107, pp. 496-501.
Dewey et al., "Bioreactor Droplets from liposome-Stabilized All-Aqueous Emulsions", Nature Communications, 2014, pp. 1-9.
Forcinti et al., "Electrostatic Effects on Protein Partitioning: Simultaneous Effect of pH and Polymer Molecular Weight", Chemical Engineering Science, 1992, vol. 47, No. 1, pp. 165-175.
Fu et al., Driving Forces for Oppositely Charged Polyion Association in Aqueous Solutions: Enthalpic, Entropic, but Not Electrostatic, Journal of American Chemical Society, vol. 138, pp. 980-990.
Fukui et al., "Preparation of Monodispersed Polyelectrolyte Microcapsules with High Encapsulation efficiency by an Electrospray Technique", Colloids Surf. A, 2010, 370(1-3), pp. 28-34.
Hann et al., "One-Step Generation of Cell-Encapsulating Compartments via Polyelectrolyte Complexation in an Aqueous Two Phase System", ACS Appl. Mater. Interfaces, 2016, vol. 8, pp. 25603-25611.
Hann et al., "Templating Polyelectrolyte Complexes at an All-Aqueous Interface" (Abstract)—1 pages.
Kaufman et al., "Soft Microcapsules with Highly Plastic Shells formed by interfacial Polyelectrolyte—Nanoparticle Complexation", Soft Matter, 2015, vol. 11, pp. 7478-7482.
Kim et al., "One-Step Generation of Multifunctional Polyelectrolyte Microcapsules via Nanoscale Interfacial Complexation in Emulsion (NICE)", ACS Nano, 2015, vol. 9, No. 8, pp. 8269-8278.
Nguyen et al., "Stabilization of Water-in-Water Emulsions by Addition of Protein Particles", Langmuir, 2013, vol. 29, pp. 10658-10664.
Ow et al., "Bright and Stable Core—Shell Fluorescent Silica Nanoparticles", Nano Letters, 2005, vol. 5, No. 1, pp. 113-117.
Peddireddy et al., "Stabilization of Water-in-Water Emulsions by Nanorods", ACS Macro Letters, 2016, pp. 283-286.
Schmaljohann, D., "Thermo—and pH Responsive Polymers in Drug Delivery", Advanced Drug Delivery Reviews, 2006, vol. 58, pp. 1655-1670.
Song et al., "All-Aqueous Electrosprayed Emulsion for Templated Fabrication to Cytocompatible Microcapsules", ACS Applied Materials & Interfaces, 2015, pp. 13925-13933.
Van Puyvelde et al., "Rheo-Optical Measurement of the Interfacial Tension of Aqueous Biopolymer Mixtures", Food Hydrocolloids, Sep. 1, 2002, vol. 16, Issue 5, pp. 395-402 (Abstract Only).
Vertegel et al., "Silica Nanoparticle Size Influences the Structure and Enzymatic Activity of Adsorbed Lysozyme", Langmuir, 2004, vol. 20, pp. 6800-6807.
Vis et al., "Water-in-Water Emulsions Stabilized by Nanoplates", ACS Macro Letters, 2015, vol. 4, pp. 965-968.
Zhou et al., "Thermoresponsive Layer-by-Layer Assemblies for Nanoparticle-Based Drug Delivery", Langmuir, 2014, vol. 30, pp. 5903-5910.

\* cited by examiner

20

210 → Inject a dispersed phase having at least a first charged component into a continuous phase having at least a second charged component, the first charged component having a charge that is opposite of a charge of the second charged component, such that a film is formed by complexation of the first charged component and the second charged component.

FIG. 1B

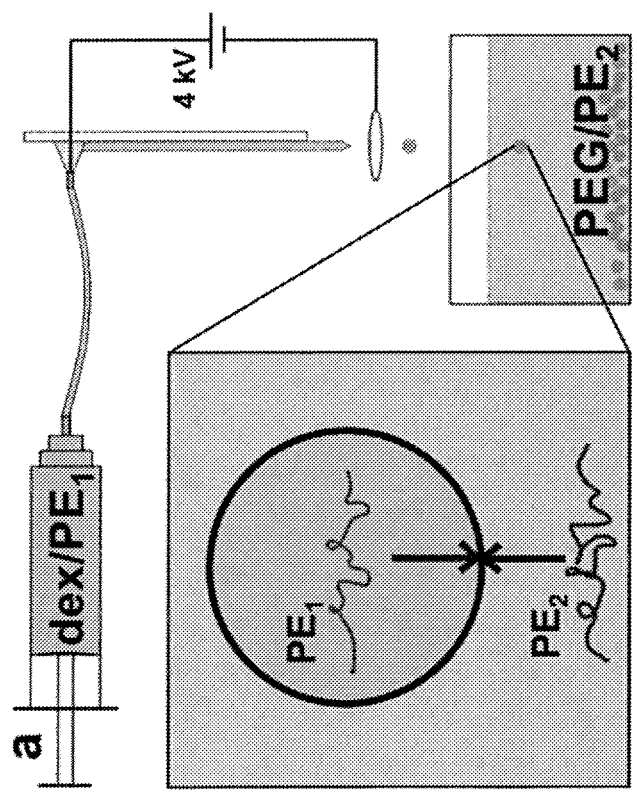
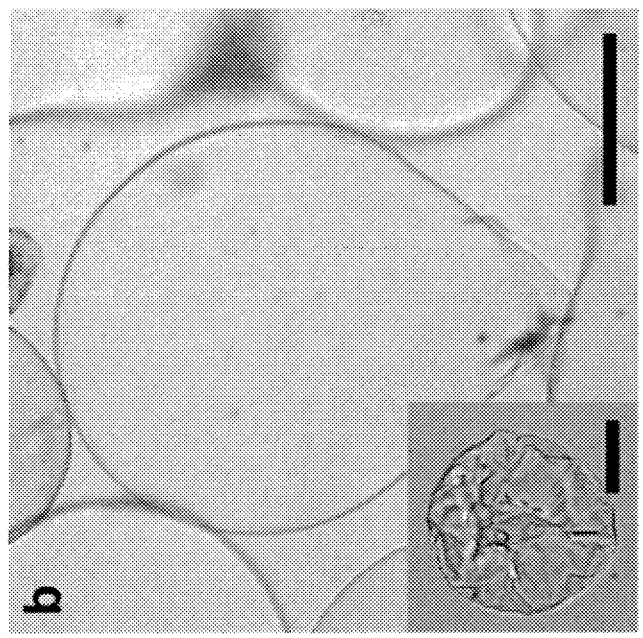
FIG. 4B
FIG. 4A

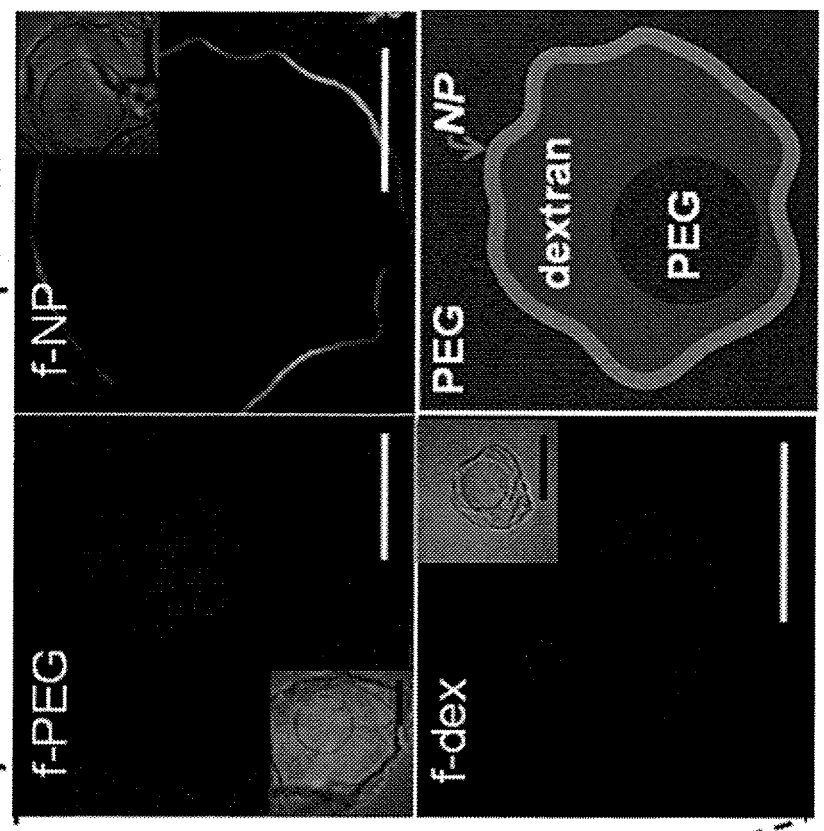
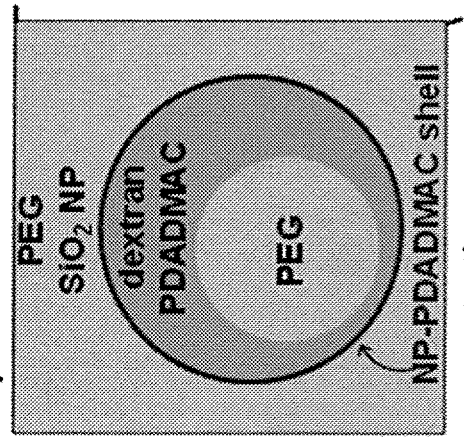
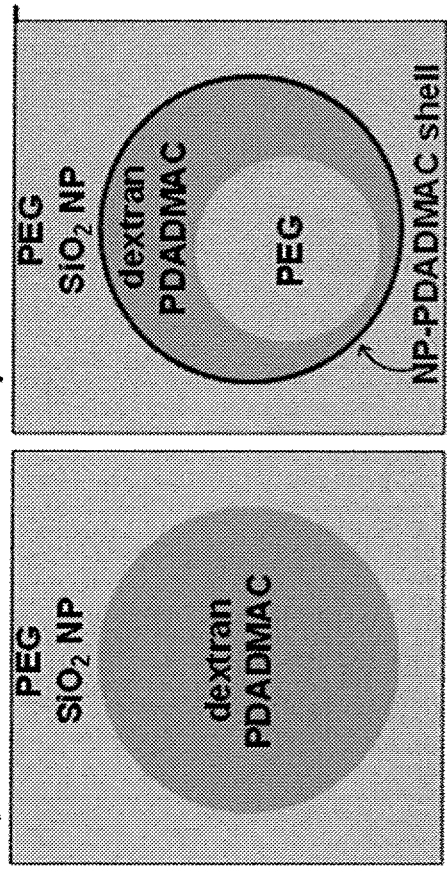
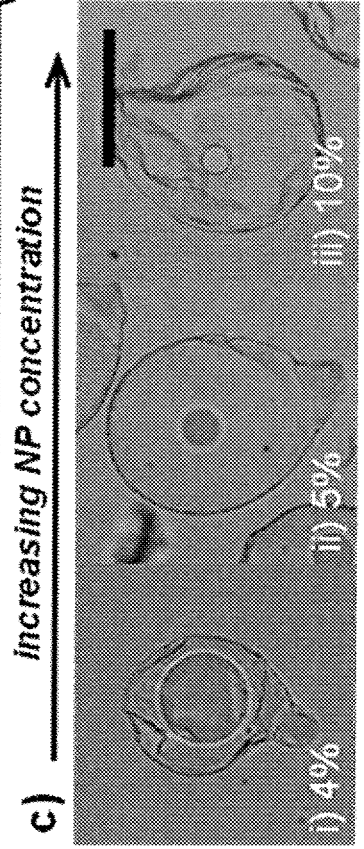
FIG. 9A  FIG. 9B  FIG. 9D
FIG. 9C

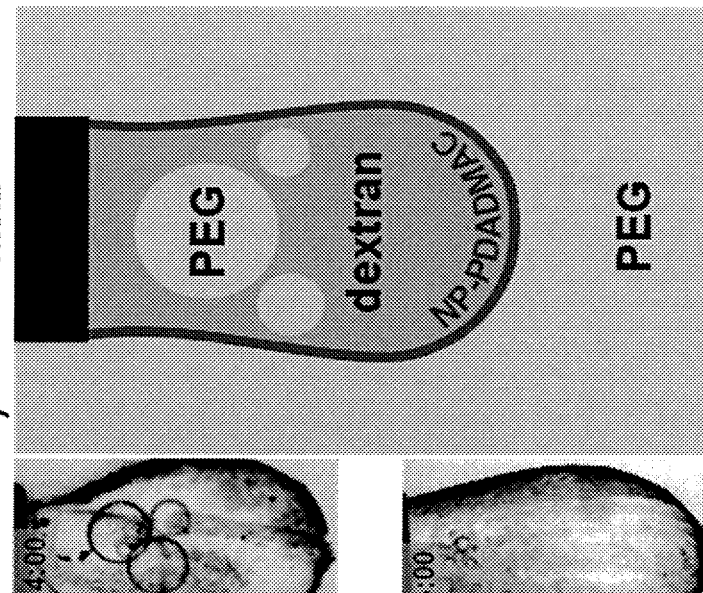
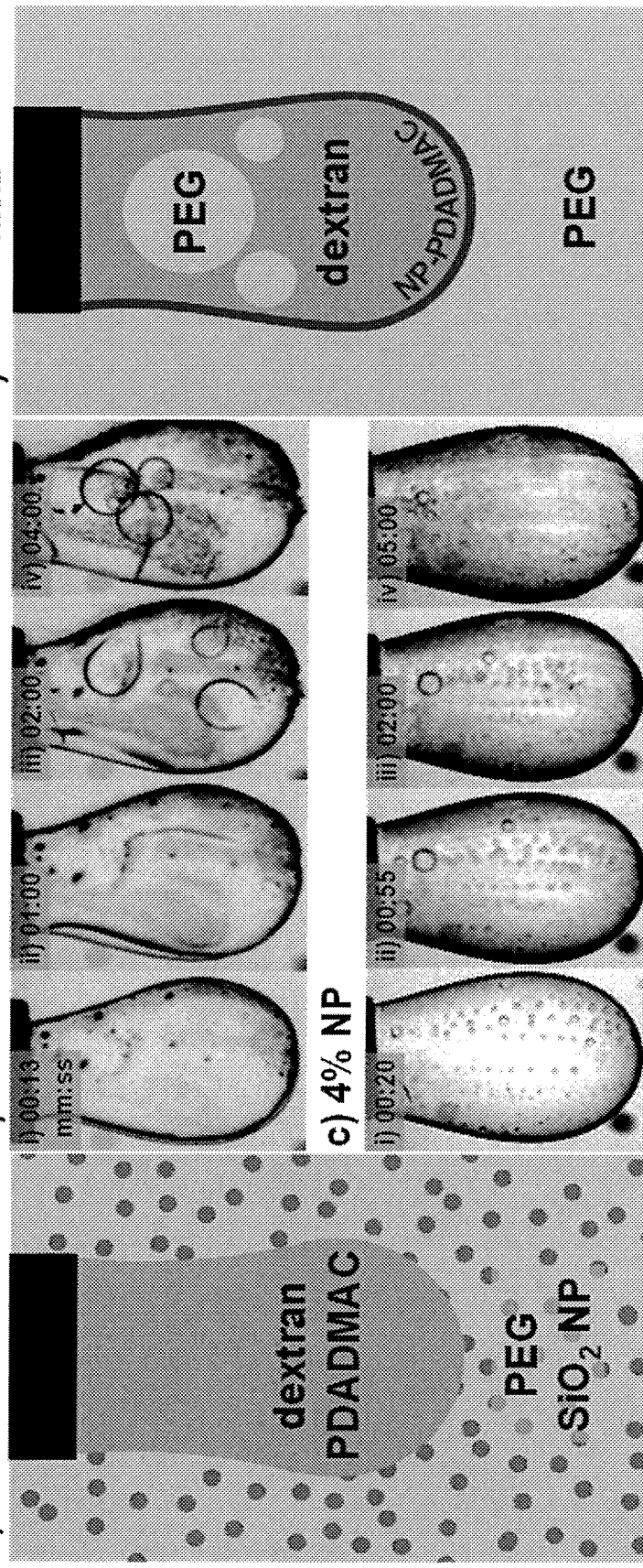
FIG. 10A  FIG. 10B  FIG. 10C  FIG. 10D

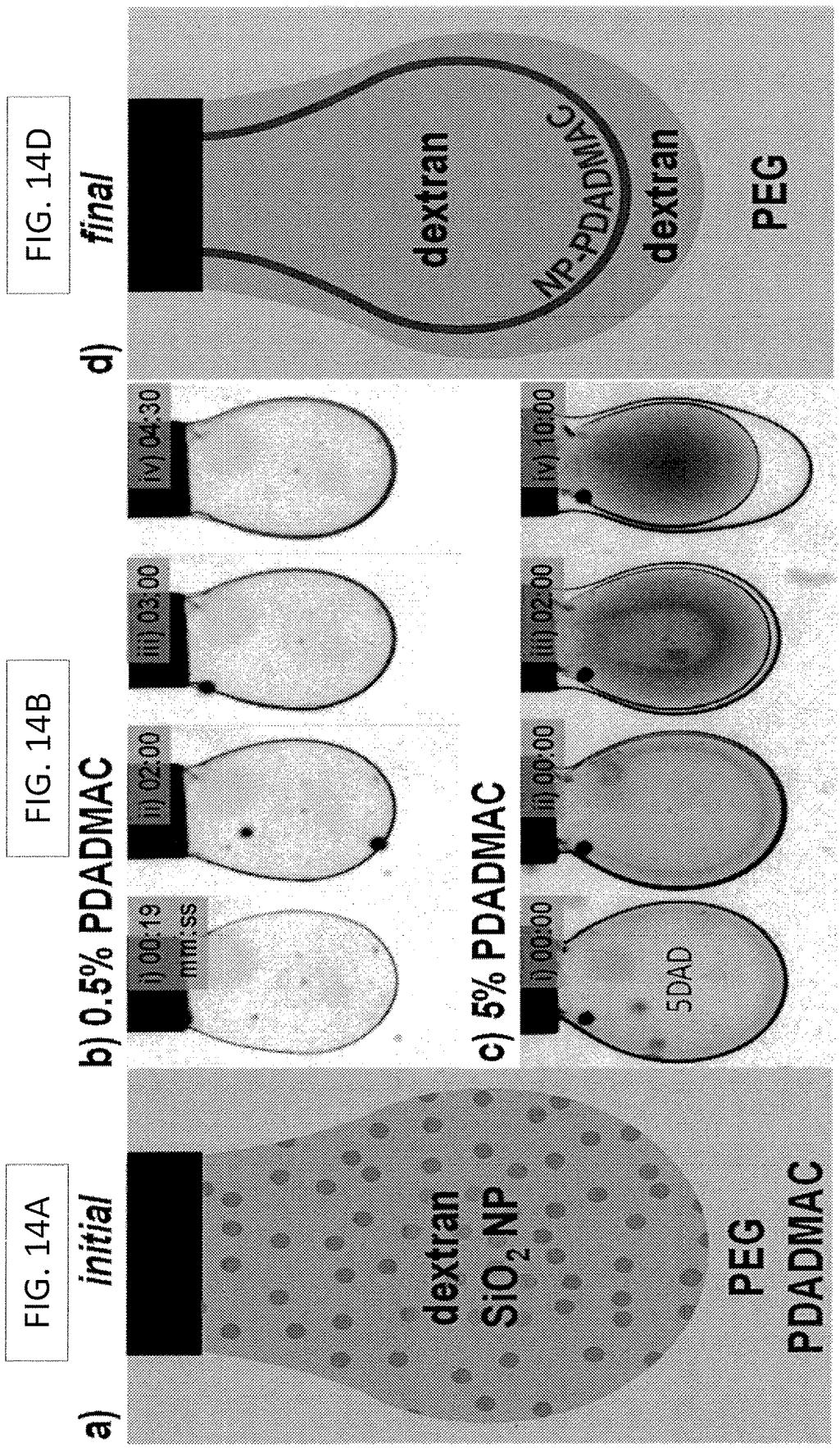

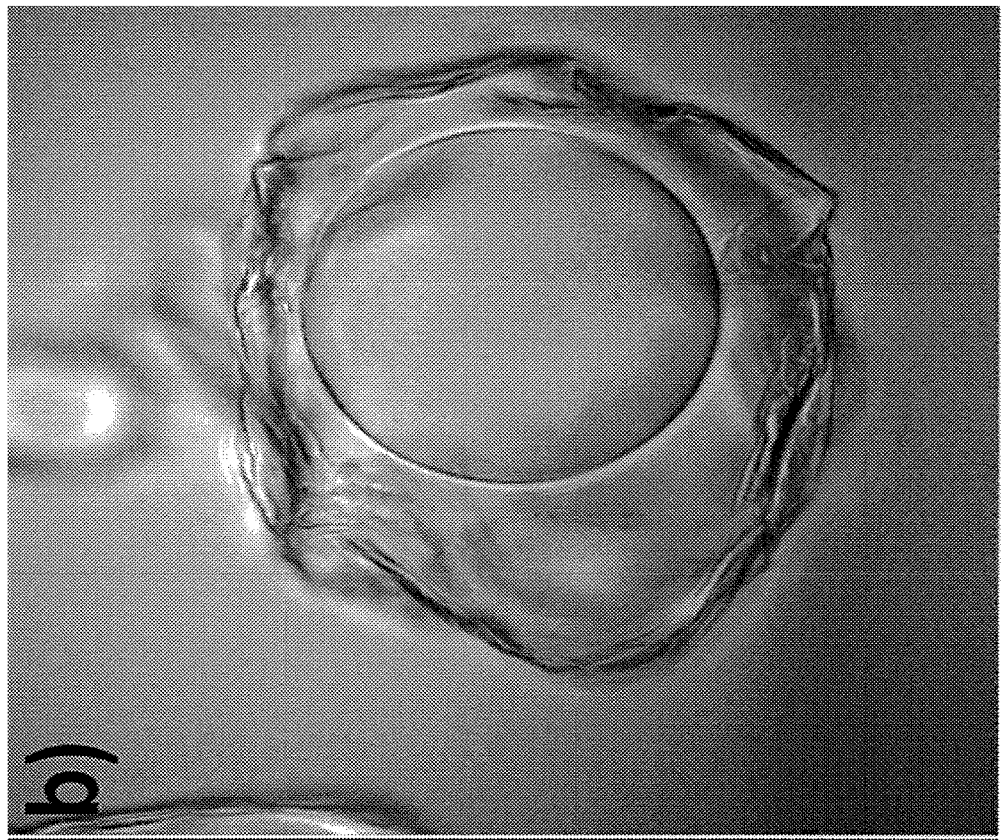
FIG. 16B
FIG. 16A

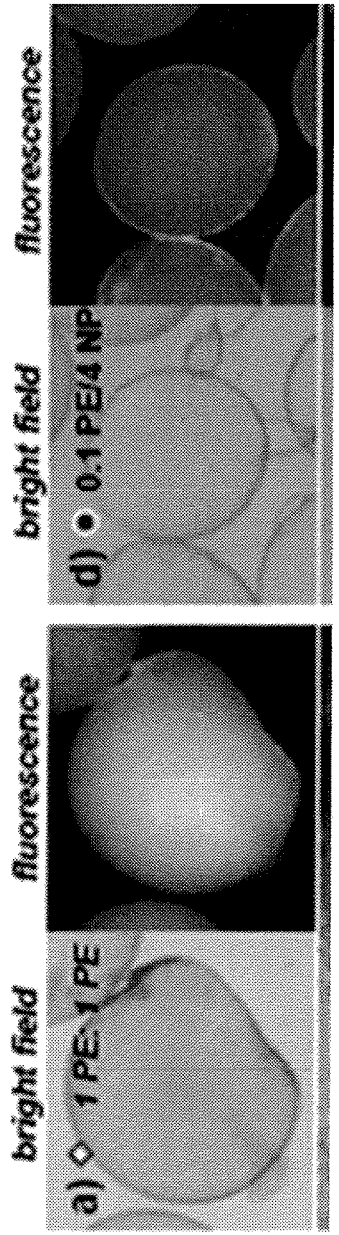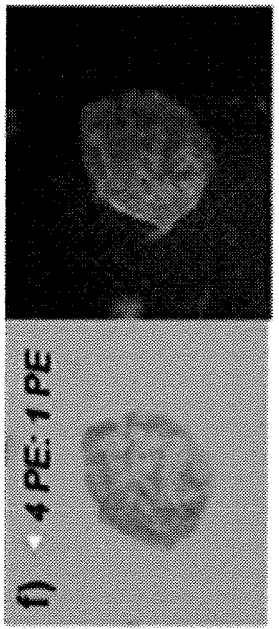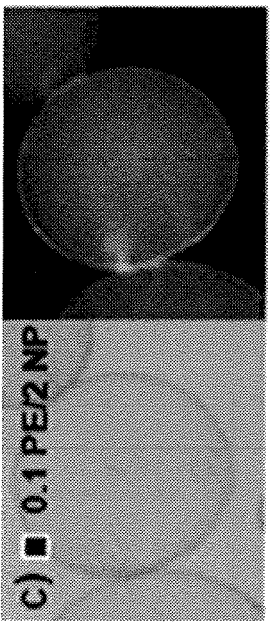

ns are incorporated herein by reference in their entireties for any and all purposes.

AQUEOUS SYSTEMS OF AT LEAST TWO PHASES CONTAINING MICROCAPSULES AND PROCESSES FOR MANUFACTURING THE SAME

RELATED APPLICATIONS

This application is a continuation of U.S. Non-Provisional application Ser. No. 15/952,321, filed Apr. 13, 2018 (now allowed), which application claims priority to and the benefit of U.S. Provisional Patent Application No. 62/486,154, filed Apr. 17, 2017. The contents of the foregoing applications are incorporated herein by reference in their entireties for any and all purposes.

GOVERNMENT RIGHTS

This invention was made with government support under 1120901 and 1055594 awarded by the National Institutes of Health. The government has certain rights in the invention.

FIELD OF THE INVENTION

This disclosure relates to aqueous systems of at least two phases having microcapsules formed therein and, more particularly, to microcapsules having a film formed by complexation of at least two mutually attractive components.

BACKGROUND OF THE INVENTION

The encapsulation of delicate, functional cargo within biocompatible microcapsules is central to diverse fields including the targeted drug delivery of pharmaceutical actives and live cell encapsulation, with applications ranging from fundamental study of microbes to the development of artificial organs. Ideally, capsules should protect, store, and allow delivery of their cargo. Thus, the encapsulating membrane should be versatile in composition and function, and the entire capsule should not comprise materials that are potentially deleterious to the contents or the spaces into which they might be implanted or introduced.

Emulsion-templated capsule formation is one method for producing microcapsules. This method exploits microcapsules in external, immiscible liquid phases. The vast majority of these systems exploit water droplets in oil, often in the form of water-in-oil emulsions.

There are, however, settings in which the oil phase may prove deleterious to cargo, in particular, if potentially toxic interactions with living cells might occur. Thus, there is a long standing need to produce microcapsules that forego the oil phase entirely.

SUMMARY OF THE INVENTION

Aspects of the invention relate to aqueous systems of at least two phases having microcapsules formed therein and processes of manufacturing the same.

In accordance with one aspect of the invention, provided is a microcapsule formed by complexation of at least two mutually attractive components. The microcapsule includes a film encapsulating a material. The film is formed by complexation of at least two mutually attractive components initially present in an aqueous dispersion comprising a continuous phase and a dispersed phase. The at least two mutually attractive components comprise at least one first component initially present in the continuous phase and at least one second component initially present in the dispersed phase.

In accordance with another aspect of the invention, provided is a process for manufacturing microcapsules in an aqueous dispersion. The process includes the step of injecting a droplet of a dispersed phase having at least a first component into a continuous phase having at least a second component, where the first component and the second component are mutually attractive, such that a film is formed by complexation of the first charged component and the second charged component.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 1B is a schematic of a process for manufacturing microcapsules in an aqueous system of at least two phases according to aspects of the invention;

FIG. 4A is a schematic illustration of system for electrospraying a dispersed phase into a continuous phase in accordance with aspects of the invention;

FIG. 4B is an image of a capsule and a reinflated capsule post-dialysis formed using the electrospray system of FIG. 4A;

FIG. 9A is a schematic illustration of the initial location of the continuous phase and dispersed phase including the charged particles therein according to aspects of the invention;

FIG. 9B is a schematic illustration of the final location of the continuous phase, dispersed phase, and complexation interface after the dispersed phase has been injected into the continuous phase in accordance with aspects of the invention;

FIG. 9C is an image of three microcapsules formed using an aqueous phase having 4% silicon dioxide, 5% silicon dioxide, and 10% silicon dioxide, respectively, according to aspects of the invention;

FIG. 9D is an image fluorescently labelled components of microcapsules in accordance with aspects of the invention;

FIG. 10A is a schematic of a pendent drop of a dispersed phase initially containing charged electrolytes into a continuous phase initially containing charged nanoparticles according to aspects of the invention;

FIGS. 10B and 10C are images of two hanging pendant drops over a period of five minutes in accordance with aspects of the invention;

FIG. 10D is a schematic of the pendent drop of FIG. 10A after a period of time;

FIG. 14A is a schematic of a pendent drop of a dispersed phase initially containing charged nanoparticles into a continuous phase initially containing charged electrolytes according to aspects of the invention;

FIGS. 14B and 40C are images of two hanging pendant drops over a period of five minutes in accordance with aspects of the invention;

FIG. 14D is a schematic of the pendent drop of FIG. 14A after a period of time;

FIGS. 16A and 16B are a fluorescent image and a bright field image, respectively, of a microcapsule fabricated with 15% dextran/0.5% PDADMAC/1 µM rhodamine tagged lysozyme into 10% PEG/4.5% 22 nm silica nanoparticles in accordance with aspects of the invention;

FIGS. 20A-20F are images of microcapsules under osmotic stress;

DETAILED DESCRIPTION OF THE INVENTION

Aspects of the present invention are directed to microcapsules formed in aqueous systems having two or more aqueous phases. The microcapsules may be formed of stable films comprising a complexation of at least two mutually attractive components. The microcapsules may be stable, such that films that do not degrade or become disrupted without the addition of a disruptor. For example, the microcapsules may be stable for at least three months, at least six months, etc., without the addition of a disruptor. Additionally and/or alternatively, the microcapsules may be configured to be robust, tunable, stimuli-responsive, and/or biologically friendly. The aqueous systems and microcapsules disclosed herein may advantageously be used for encapsulating delicate or functional cargo for uses in, e.g., drug delivery, live cell encapsulation, microbial research, etc.

Additional aspects of the present invention are directed to processes for producing the microcapsules and the aqueous systems. In one embodiment, the process for producing the microcapsules in the aqueous system includes a single step. The processes disclosed herein, advantageously, do not require layer by layer addition of polyelectrolytes to form the microcapsules.

According to one embodiment of the invention, microcapsules include a film formed by complexation of at least two mutually attractive components initially present in an aqueous dispersion comprising a continuous phase and a dispersed phase. Preferably, at least one first component is initially present in the continuous phase and at least one second component is initially present in the dispersed phase.

As used herein, the term "mutually attractive components" refers to components attracted to each other by one or more forces including, but not limited to, ionic forces, hydrogen bonding, intermolecular forces, metal coordination, host-guest interactions, etc. In one embodiment, the two mutually attractive components are attracted to each other due to opposite electrical charges. Although one or more embodiments disclosed herein may describe the mutually attractive components as charged components, attracted to each other by way of ionic charges, the components may be adapted to be attracted to each other by way of hydrogen bonding, metal coordination, host-guest interactions or other forces.

Figure 1A:
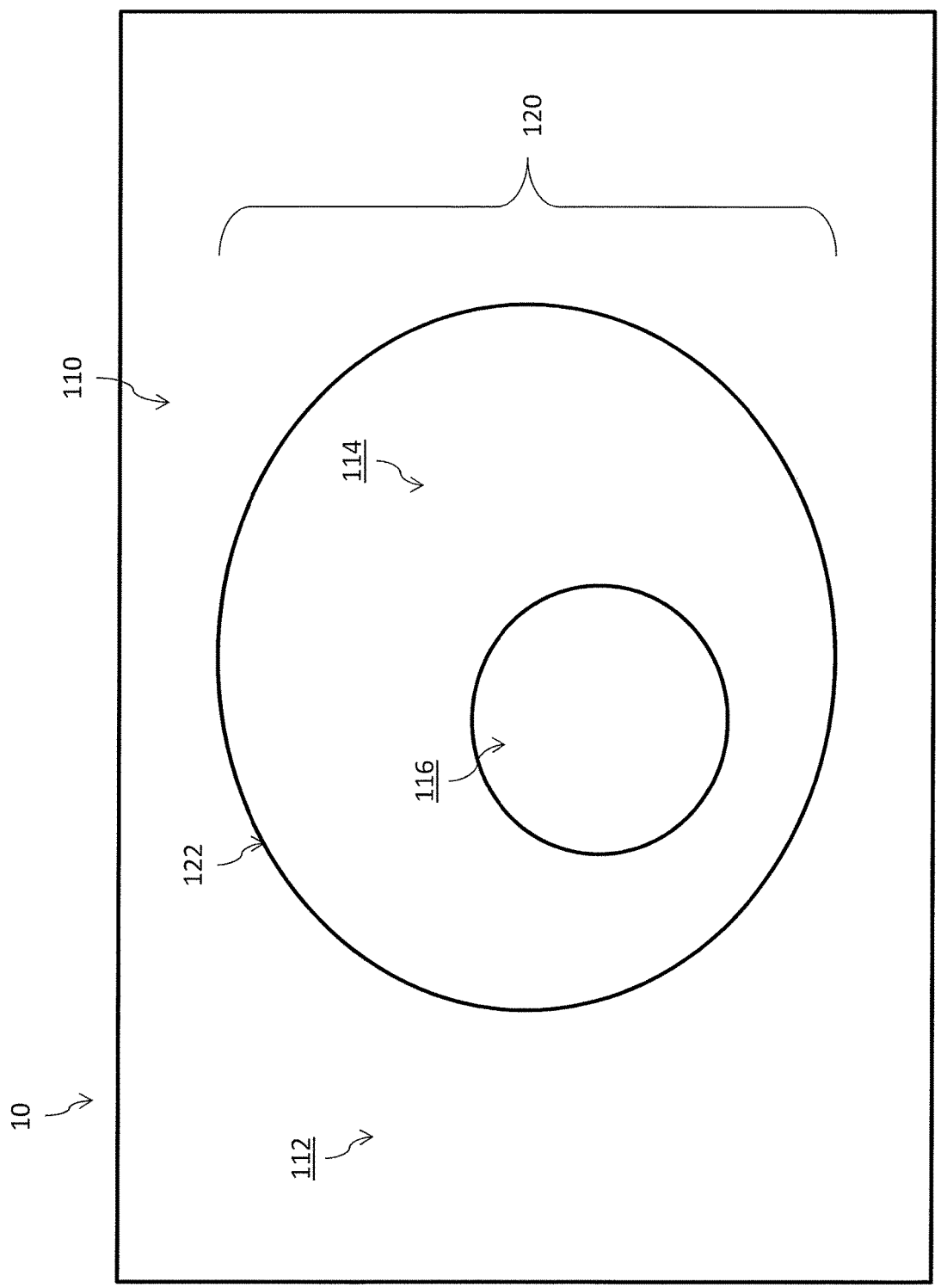
FIG. 1A is a schematic of an aqueous systems of at least two phases having a microcapsule formed therein in accordance with aspects of the invention.

FIG. 1A illustrates an aqueous system 10 comprising microcapsules 120 formed in an aqueous dispersion 110. Aqueous dispersion 110 comprises a continuous phase 112 and a dispersed phase 114. Continuous phase 112 has an aqueous composition that may be rich in a hydrophilic compound. For example, the composition of continuous phase 112 may contain polyethylene glycol ("PEG"). In one embodiment, continuous phase 112 has a composition comprising at least 10% PEG by weight, at least 12.5% PEG by weight, at least 15% PEG by weight, etc. Continuous phase 112 may have a composition having 90% or less of water, 87.5% or less of water, 85% or less of water, etc.

Dispersed phase 114 has an aqueous composition that may be rich in a different hydrophilic compound. Preferably, the composition of dispersed phase 114 is dissimilar from the composition of continuous phase 112, such that upon contact of the dispersed phase 114 and continuous phase 112, the majority of the dispersed phase forms a thermodynamically stable phase. For example, the composition of continuous phase 112 may contain dextran. In one embodiment, dispersed phase 114 has a composition comprising at least 10% dextran by weight, at least 12.5% dextran by weight, at least 15% dextran by weight, etc. Dispersed phase 114 may have a composition having 90% or less of water, 87.5% or less of water, 85% or less of water, etc. Although continuous phase 112 may be described herein as PEG rich and dispersed phase 114 as dextran rich, in one embodiment, the continuous phase is dextran rich while the dispersed phase is PEG rich.

Microcapsules 120 include a film 122 encapsulating a material. The encapsulated material includes at least one of dispersed phase 114 and continuous phase 112, and may also include desired compounds, molecules, functional cargo, drug compounds, bacteria, living cells, etc. Film 122 is formed by complexation of at least two charged components initially present in continuous phase 112 and dispersed phase 114, where the first component is initially present in continuous phase 112 and the second component is initially present in dispersed phase 114. Each of the at least two charged components has a diffusive flux in aqueous dispersion 110. The diffusive flux of each charged component may be based on the charge and concentration of each of the charged components and may be determined, e.g., using Fick's law. Accordingly, a charged component having a high concentration may have a diffusive flux that is equal to the diffusive flux of a charged component having a lower concentration but a higher charge. The diffusive flux of each of the charged components may be balanced, such that a stable film 122 is formed. In one embodiment, a stable film will not degrade and/or change shape unless a solution condition is changed, e.g., pH, ionic strength, etc. For example, the ratio of the diffusive fluxes may be considered substantially balanced from 2:1 to 1:2. Preferably the ratio of the diffusive fluxes ranges from 1.5:1 to 1:1.5, and more preferably from 1.25:1 to 1:1.25. In one embodiment, the ratio of the first charged component to the second charged component produces a diffusive flux of the first charged component that is substantially similar to the diffusive flux of the second charged component. For example, the charge ratio of the first charged component to the second charged component may range, e.g., from 1:2 to 2:1, from 1:1.5 to 1.5:1, from 1:1.25 to 1.25:1, etc.

Figures 2A, 2B, 2C:
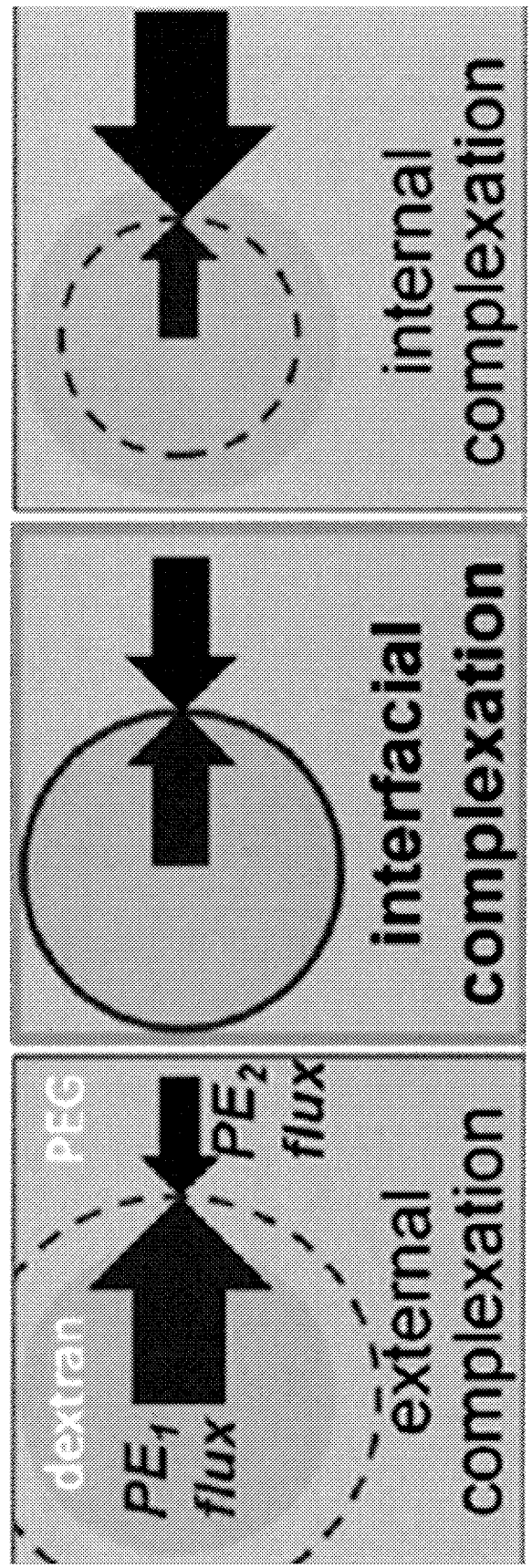
FIGS. 2A-2C are illustrations of complexation between two components formed by external complexation, interfacial complexation, and internal complexation, respectively, in accordance with aspects of the invention.
Figure 3A:
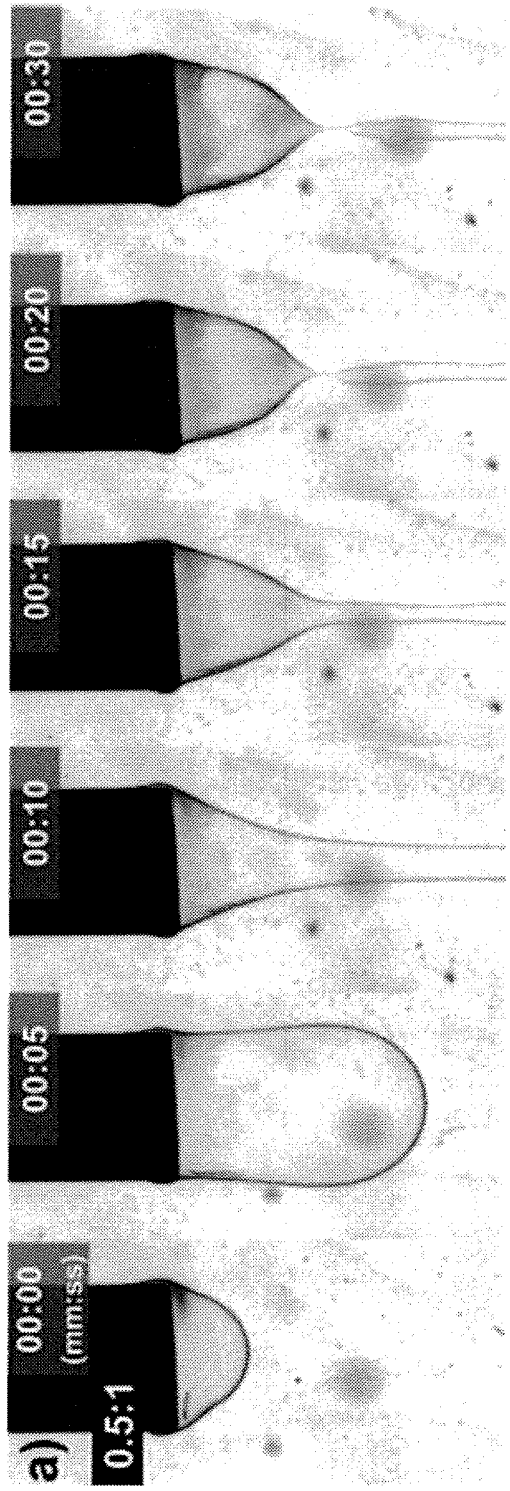
FIGS. 3A-3D are images of a dispersed phase being injected into a continuous phase at various times according to aspects of the invention.
Figure 3B:
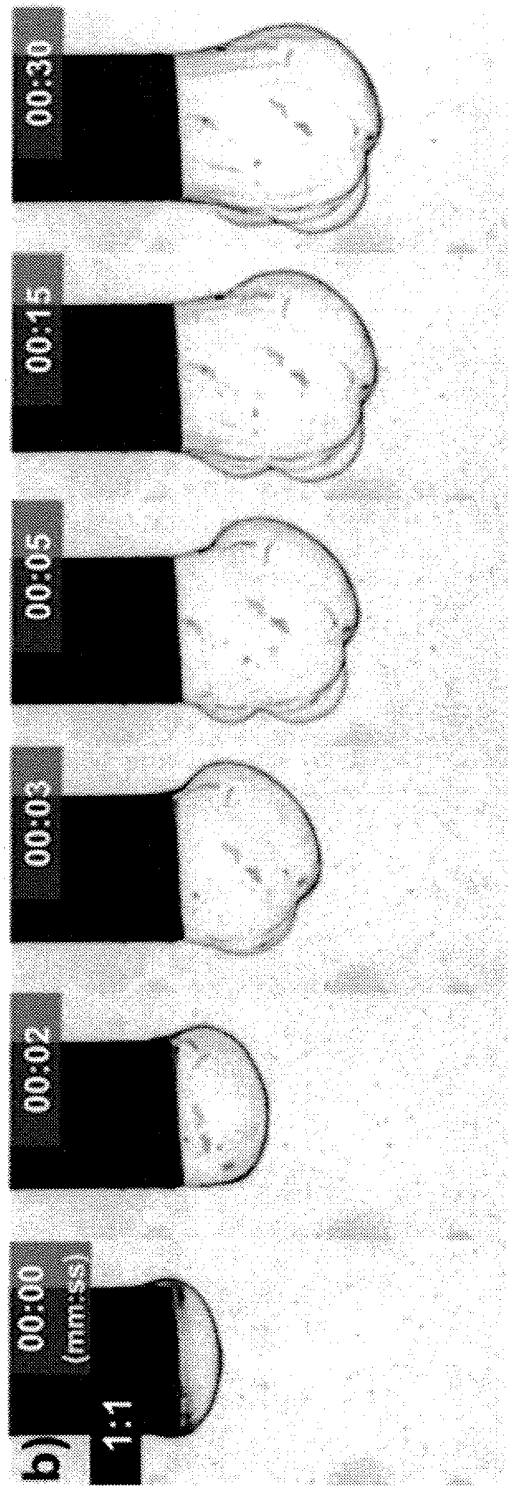
Figure 3C:
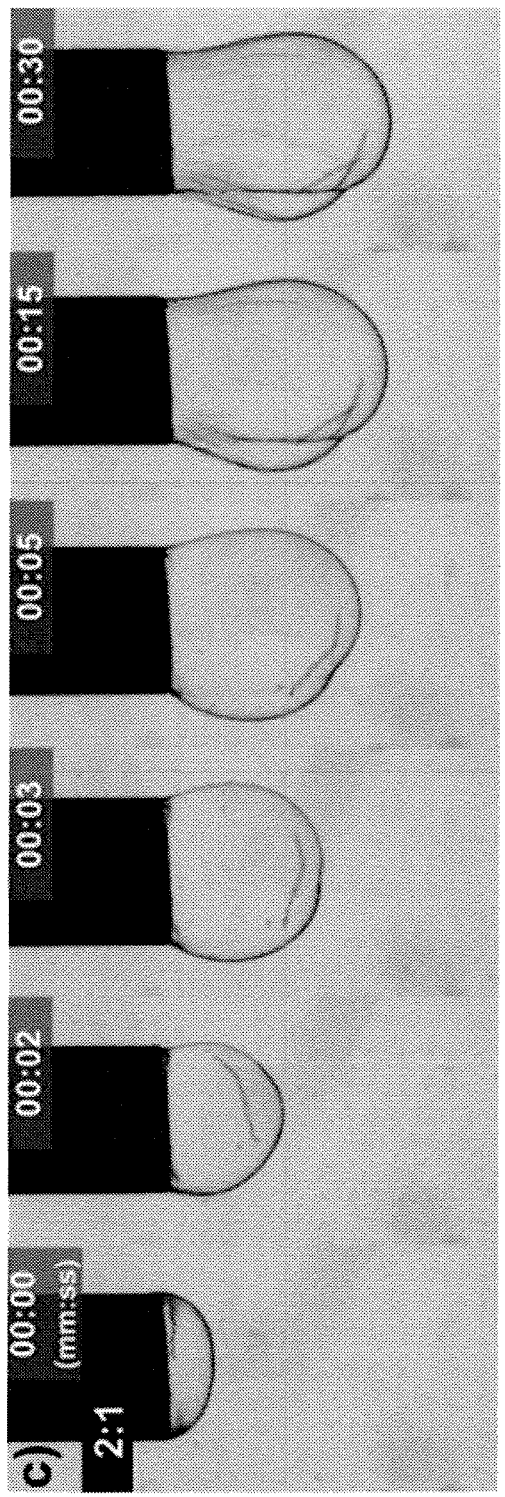
Figure 3D:
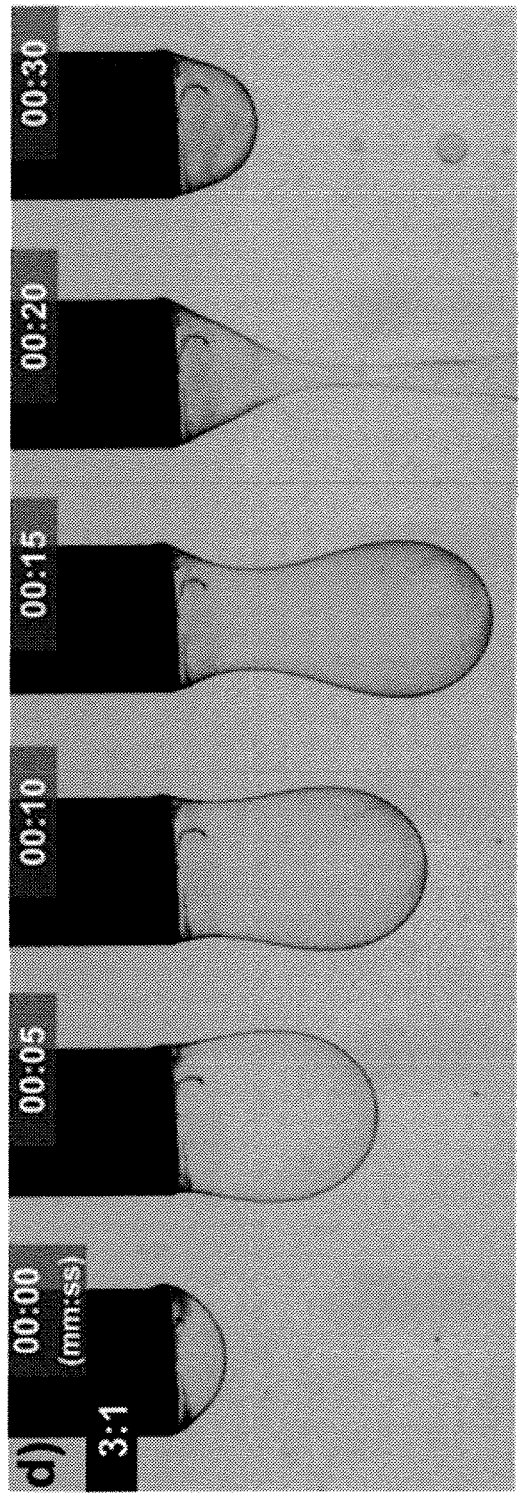

Microcapsules 120 may be configured such that the complexation and, thus, the formed film 122 is proximal to the interface of the continuous phase and the dispersed phase. In one embodiment, however, the complexation occurs in continuous phase 112, as shown in FIG. 2A, or dispersed phase 114, as shown in FIG. 2C. Advantageously, the location of the complexation may be varied by adjusting at least one of the diffusive flux of each of the charged components, the concentration of each of the charged components, or the viscosity of continuous phase 112 and/or dispersed phase 114. Additionally and/or alternatively, different charged particles may be used to adjust the location of the complexation.

The at least two charged components forming film 122 include at least one first charged component initially present in continuous phase 112 and at least one second charged component initially present in the dispersed phase 114. The first charged component has a charge that is opposite of the charge of the second charged component, such that complexation occurs between the first charged component and the second charged component. The first charged component and/or the second charged component may be an electrolyte (e.g., polyelectrolyte) or a nanoparticle. For example, the first charged component may be a charged electrolyte while the second charged component may be an oppositely charged electrolyte. Suitable electrolytes include, but are not limited to, Polyacrylic acid, polyallylamine hydrochloride, poly(sodium 4-styrenesulfonate) ("PSS"), poly(diallyldimethylammonium chloride) ("PDADMAC"), polyethyleneimine, polyvinylamine, polymethacrylic acid, etc. In one embodiment, the first charged particle is a poly(sodium 4-styrenesulfonate) group located within continuous phase 112, while the second charged particle is a poly(diallyldimethylammonium chloride) group located within dispersed phase 114. In another embodiment, continuous phase 112 contains a poly(diallyldimethylammonium chloride) group, while dispersed phase 114 contains a poly(sodium 4-styrenesulfonate) group.

Film 122 may be formed by complexation of a charged electrolyte and an oppositely charged nanoparticle. The nanoparticle may be initially contained within continuous phase 112 or dispersed phase 114, while the oppositely charged electrolyte is initially contained within the other phase of aqueous dispersion 110. Advantageously, two phase aqueous systems or three phase aqueous systems may be produced using a complexation of a charged electrolyte and a nanoparticle.

For example, a two phase aqueous system may be produced by forming microcapsules 120 having a film within dispersed phase 114 by initially containing the charged nanoparticle within dispersed phase 114 and the charged electrolyte within continuous phase 112. Alternatively, a three phase aqueous system may be produced by forming microcapsules 120 having internal aqueous phase 116 within dispersed phase 114. Microcapsule 120 may be configured to have internal aqueous phase 116 and an interface complexation film 122 by initially containing the charged nanoparticle within continuous phase 112 and initially containing the charged electrolyte in dispersed phase 114. Preferably, to form internal phase 116, continuous phase 112 is adapted to have an osmotic pressure that is greater than an osmotic pressure of dispersed phase 114. In one embodiment, the transfer of water molecules from dispersed phase 114 to continuous phase 112 is proportional to the transfer of continuous phase 112 into microcapsule 120 and/or dispersed phase 114. In another embodiment the difference in osmotic pressure between continuous phase 112 and dispersed phase 114 is adapted such that the amount of continuous phase 112 transferred into microcapsule 120 is at least 5% by volume, preferably at least 10% by volume, more preferably at least 20% by volume, etc., of the total volume within microcapsule 120. The difference in osmotic pressure between continuous phase 112 and dispersed phase 114 may be varied based on the amount of nanoparticles, e.g., $SiO_2$, within the aqueous dispersion 110.

Film 122 may be configured to be rigid and/or permeable based on the charged nanoparticles. For example, film 122 may be configured to have a desired rigidity by increasing the concentration and/or size of the charged nanoparticles. In one embodiment, film 122 is formed to be rigid, such that film 122 cannot be inflated to remove wrinkles using negative osmotic stress. Additionally and/or alternatively, the permeability of film 122 may be adjusted by increasing or decreasing at least one of the concentration and/or size of the charged nanoparticles.

The charged nanoparticles may comprise an oxide functional group. For example, the charged nanoparticles may comprise a mineral oxide, such as, e.g., aluminum oxides, titanium oxides, etc. Other suitable nanoparticles may include, but not be limited to, catalytic nanoparticles such as silver, gold, etc. In one embodiment, the charged nanoparticles comprise a silicon oxide ("$SiO_2$"). The charged nanoparticles may have a strong preference for either continuous phase 112 or dispersed phase 114. In one embodiment, the charged nanoparticle has a strong preference for a PEG rich composition, such that the charged nanoparticles do not flux into a dextran rich phase.

Film 122 may be formed by complexation of two or more oppositely charged electrolytes and one or more charged nanoparticles. For example, the structure and properties of microcapsules 120 formed via complexation in aqueous dispersion 110 may be tuned by inducing assembly between the continuous phase 112, which may contain at least one charged electrolyte and at least one charged nanoparticle of the same charge, and a dispersed phased 114 containing an oppositely charged electrolyte. By forming microcapsules 120 using two or more oppositely charged electrolytes and one or more charged nanoparticles, microcapsules 120 may advantageously include a film having the functionality of films formed by complexation of charged electrolytes and nanoparticles as well as the enhancement of mechanical properties typical of films formed by complexation of two charged electrolytes.

FIG. 1B illustrates a process 20 for forming microcapsules in an aqueous dispersion. Process 20 may advantageously include a single step (e.g., step 210) for producing microcapsules having a film formed by the complexation of a first charged component and a second charged component.

In step 210, a dispersed phase composition having at least a first charged component is introduced and/or injected into a continuous phase composition having at least a second charged component. The first charged component is adapted to have a charge that is opposite of a charge of the second charged component, such that a film is formed by complexation of the first charged component and the second charged component. In one embodiment, the dispersed phase is injected into the continuous phase by way of electrospraying. Additionally and/or alternatively, the dispersed phase may be introduced into the continuous phase using any known technique for forming dispersions, such as, e.g., using a needle, microinjectors, pendant drops, electrospraying, etc., within a continuous phase without prematurely complexing the charged particles.

Process 20 provides several advantages, such as increased robustness, simplicity, and an greater ability to modify the resulting aqueous systems and/or microcapsules. For example, process 20 may enable controlling the porosity of the microcapsule by adjusting the concentration of the first charged component, the second charged component, or a combination thereof. The rigidity may also be controlled by adjusting at least one of a concentration and a particle size of the first charged component, the second charged component, or a combination thereof. Process 20 also enables the diffusive flux of the first and second charged components to be controlled, such that the first diffusive flux may balance the second diffusive flux. Additionally and/or alternatively, the osmotic pressure of continuous phase and/or the osmotic pressure of dispersed phase may be controlled by adjusting the amount and/or concentration of nanoparticles, e.g., $SiO_2$, within the aqueous dispersion.

Process 20 may include an additional step of disrupting the microcapsules by adding a disruptor. For example, if the microcapsule produced during step 210 has a film formed by complexation of a charged electrolyte and a nanoparticle, a disruptor comprising a salt compound or an acid may be added to the aqueous dispersion to degrade the microcapsules. In one embodiment, the microcapsules produced during step 210 are degraded by reducing the pH of the aqueous dispersion to a pH of 5 or less. By way of another example, if the microcapsule produced during step 210 has a film formed by complexation of two charged electrolytes, a disruptor comprising water molecules may be added to the aqueous dispersion to degrade the microcapsules. Thus, the use of a disruptor may allow for the controlled release of the material within the microcapsule.

The following examples are non-limiting embodiments of the present invention, included herein to demonstrate the advantageous results obtained from aspects of the present invention.

Example 1—Polyelectrolyte Complexation in Two Phase Systems

An aqueous two phase system ("ATPS") having microcapsules of poly-(ethylene glycol) ("PEG") and dextran were produced. The Poly(ethylene glycol) (PEG, MW=20 000 g/mol), dextran from *Leuconostoc* spp. (MW=450 000-600 000 g/mol), poly(diallyldimethylammonium chloride) (PDADMAC, 20 wt % MW=200 000-350 000 g/mol and MW=400 000-500 000 g/mol), and poly(sodium 4-styrenesulfonate) (PSS, MW=70 000 g/mol) were purchased from Sigma-Aldrich™. Fluorescein-labeled PSS (f-PSS) was synthesized. Rhodamine B-tagged dextran (RD70, MW=70 000 g/mol) was purchased from ThermoFisher Scientific™. All chemicals were used as received.

All solution composition % are given in wt %. A stock solution of 20% dextran was prepared by stirring (DI) water from a Millipore Milli-Q unit (>18.2 MΩ cm) with the appropriate amount of dextran on a stir plate overnight. This stock solution was subsequently mixed with aqueous solutions of either 20% PDADMAC or 20% PSS, to which the remaining mass of DI water was added to achieve the desired polyelectrolyte (PE) concentration. A similar process was followed for the continuous PEG phase; a stock solution of 15% PEG was prepared by overnight mixing with DI water, and the respective amounts of PE and water were added to achieve the desired PE concentration.

Pendant drops were injected using an Attension Theta optical tensiometer. A needle of 0.85 mm diameter injected 1 µL of 15% dextran/0.5% PDADMAC (MW 400 000-500 000) at a rate of 1 µL/s into a cuvette containing 3 mL of 10% PEG/PSS solutions. Recording of the drop was started as the drop was being injected at a rate of 6 frames/s.

Capsules were made using an all-aqueous electrospray technique. Briefly, 15% dextran droplet phases were prepared with either 0.5% PDADMAC (MW 200 000-350 000) or 0.64% PSS. This solution was loaded into a syringe and connected to tubing which is, in turn, connected to a tapered capillary with a tip diameter of 130 µm. The dextran solution was charged by connecting the inlet needle to one electrode from a high voltage power source. The opposite electrode was connected to a 2 cm-diameter copper ring placed 1 mm from the tip of the tapered capillary. This arrangement applies the complementary electric force which pulls the micron-scale droplets out of the capillary. The droplets were fabricated at a flow rate of 1 mL/h with an applied voltage of 4.8 kV. For encapsulation of bacteria, the diameter of the capillary tip was 70 µm, and droplets were fabricated at a flow rate of 4 mL/h with an applied voltage of 4 kV. These droplets were sprayed into the 10% PEG solution with the oppositely charged polyelectrolyte. Polyelectrolyte concentrations are defined based on molar charge ratios of the two polyelectrolytes. Both polyelectrolytes used in this study contribute one charge per repeat unit. For example, the molar charge ratio of a 1:1 solution corresponds to 1 mol of each polyelectrolyte, 207 g PSS/161.5 g PDADMAC, or 1.28 g PSS/1 g PDADMAC. In this example, for a dispersed phase of 15% dextran/0.5% PDADMAC, the continuous phase is 10% PEG/0.64% PSS to achieve the 1:1 molar charge ratio.

Experiments were performed within microdialysis cells to probe the release properties of capsules in response to changes in the ionic strength of the solution. Polycarbonate track-etched (PCTE) membranes (1 µm pores) were used to allow passage of water and salt solutions between the two chambers of the microdialysis cell. Total intensity loss of RD70 was measured by averaging the fluorescent intensity of monitored capsules in ImageJ at different time points and normalizing by initial time intensity. Initial time t=0 marked the time at which the bulk solution within the microdialysis cell was exchanged.

Capsules containing bacteria were created by mixing 15% dextran, 0.64% PSS, 20 µL/mL *Pseudomonas aeruginosa* (PAO1; OD 0.02; ~107 CFU/mL), and cell culture medium. The cell culture medium was added to the polymer mixture to achieve a total concentration of 0.64% PSS and 15% dextran. The medium was 2% glucose and 1% minimum medium supplement. After electrospraying into 10% PEG, 0.5% PDADMAC solution, the capsules were moved to a separate bath of 15% dextran, 25% medium by pipetting. These capsules were then incubated at 37° C. overnight to assess growth of PAO1. When imaging, 2 mL aliquots of capsule solution were moved to a coverslip-bottom Petri dish and 1.5 µL of 3.34 mM SYTO 9 and 20 mM propidium iodide dyes were added to the solution. All imaging of bacterial capsules were done with an confocal laser scanning microscope (CLSM). Bacterial cells were counted using the Analyze Particles function within ImageJ.

The microcapsules had a complexation of two oppositely charged strong polyelectrolytes, poly(styrenesulfonate) (PSS) and poly(diallylmethylammonium chloride) (PDADMAC). Each polyelectrolyte was initially present in either the drop phase, comprising a solution of 15% dextran in water, or the external phase, comprising a solution of 10% PEG in water. The drop and external phase compositions were quite close to one of the equilibrium conditions in the ternary phase diagram of this APTS (15.54% dextran, 0.55% PEG and 9.51% PEG, 0.05% dextran), so that, when the two solutions come in contact, chemical potential gradients driving intermixing of the PEG and dextran solutions are weak. The strong polyelectrolytes dissociate fully in aqueous solution and remain fully ionized regardless of the solution pH and ionic strength, facilitating the systematic investigation of their complex formation. Complex formation on drops containing a fixed concentration of 0.5% PDADMAC in external PEG solutions containing various % PSS were selected to achieve charge ratios of PSS/PDADMAC ranging from 0.5:1 to 3:1, where 1:1 corresponds to 0.64% PSS.

As preliminary research regarding the rich behaviors within ATPSs, the complexation on pendant drops of the dextran solution formed in the external PEG solution from a needle 0.85 mm in diameter were studied. As the drops were injected, they were recorded at a rate of 6 frames/s. Snapshots from these video series (illustrated in FIGS. 3A-3D), reveal highly nonmonotonic changes in interfacial complexation with charge ratio. The 0.5:1 drop elongates and detaches. The Bond number ("BO")=$(\Delta \rho\ g\ R_N^2)/\gamma$ characterizing the importance of gravitational forces to interfacial forces is much greater than unity, where g is the gravitational acceleration constant, $\Delta\rho$ is the density difference between the phases, RN is the characteristic length scale (i.e., droplet size), and $\gamma$ is the interfacial tension. This indicates that, absent the formation of a complexed elastic structure to stabilize the drop interface, the drop will elongate and detach from the needle rather than attain a stable shape. This suggests that, at this charge ratio, any complex at the interface is too weak to stabilize the drop. At higher charge ratios (1:1 and 2:1), the drop interfaces are complexed within the first frames, and the drops remain stably attached to the tip of the needle. Also, the irregular shapes of these drops suggest the formation of elastic layers stabilizing the interfaces. By increasing the charge ratio even further to 3:1, however, the dextran drop is no longer stabilized and again falls off due to gravity.

To understand these trends, it is helpful to note that, in the system of this Example, not only were there very weak trapping energies at the interface, but both polyelectrolytes were miscible in both phases. This is a strikingly different feature than in the oil-water systems, in which interfaces trap the film forming components, and components of differing solubilities in drop and external phases are commonly exploited. In this system, a polyelectrolyte in one phase can freely diffuse into the other phase, unless it is captured by the counter-polyelectrolyte to form a stable complex. This suggests that complexation may not be limited to the water/water interface. Instead, the relative fluxes of the two polyelectrolytes determine the location of complex formation and that this location can be tuned to form stable interfacial complexes. If they are imbalanced, complexation occurs in either the drop or external phases. In FIGS. 3A-3D, the fluxes of the two polyelectrolytes are optimum between 1:1 and 2:1, which results in a stabilized film, whereas the charge ratios of 0.5:1 and 3:1 have imbalanced polyelectrolyte fluxes, allowing complexes to form out of and into the drop, respectively. Mass transport within this system was determined by both convection and diffusion and quantitative modeling to diagnose the specifics of the transport mechanisms that influence the formation of microcapsules and particles.

Figure 4D:
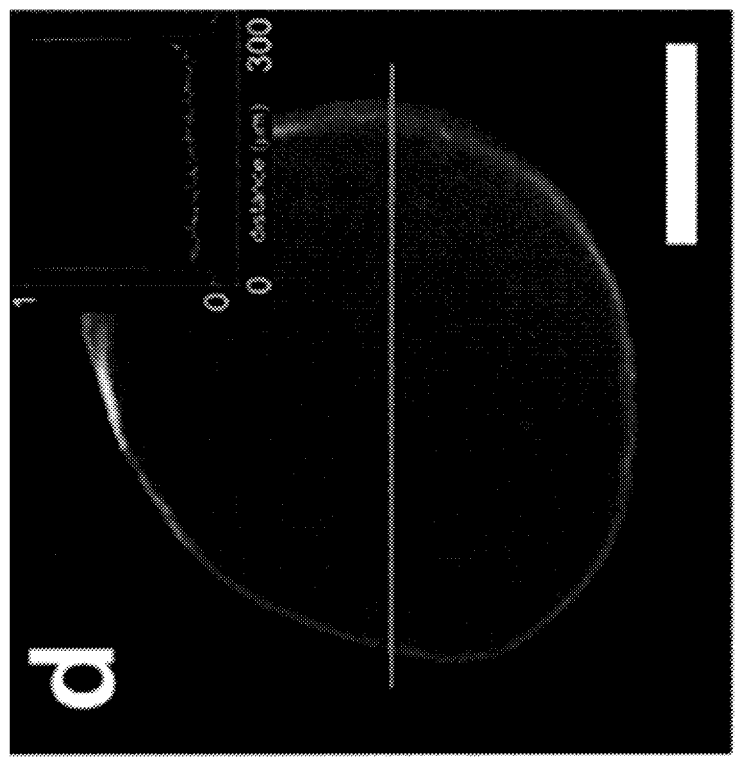
FIGS. 4C and 4D are images of microcapsules formed according to aspects of the invention.
Figure 4C:
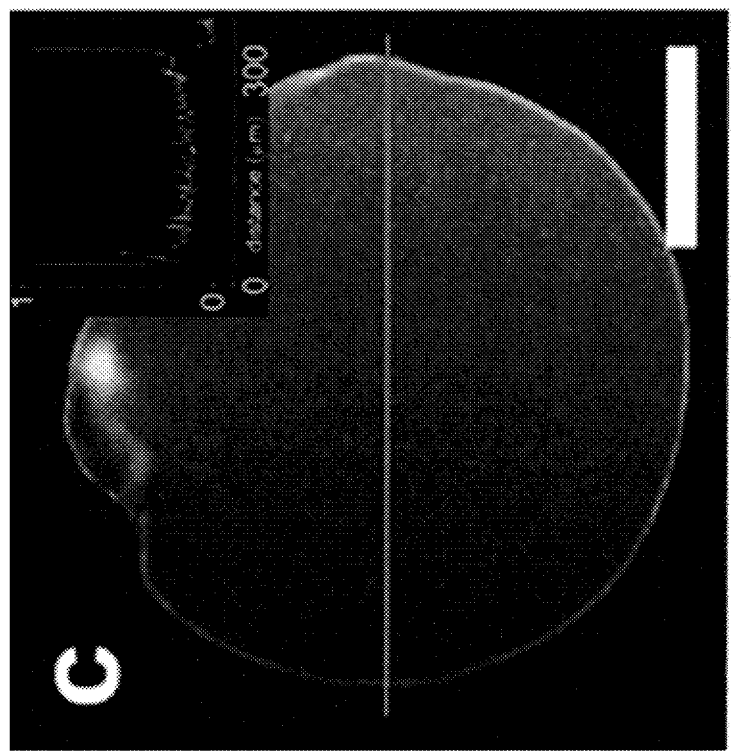

In view of the above, microcapsules were formed around small droplets. Dextran-containing aqueous droplets roughly 200 μm in diameter were formed by all aqueous electrospray ("AAE") into an external bath containing PEG; the drop phase contains one polyelectrolyte, the PEG phase the other. AAE relies on the formation and breakup of an aqueous jet under a high voltage, allowing for the preformed droplets to meet the continuous phase with neat interfaces between the two phases (e.g., FIG. 4A). Under appropriate conditions hollow microcapsules with many wrinkles were formed (e.g., FIG. 4B). The formation of wrinkles on the microcapsules was likely due to the mismatch of osmotic pressures between the two phases and can be removed by dialyzing the capsules against DI water to induce an influx of water, as shown in FIG. 4B. The integrity of the microcapsules and their ability to encapsulate molecules can be demonstrated by adding rhodamine-labeled dextran (MW=70 000) in the droplet phase of the ATPS as shown in FIG. 4C. Moreover, robust hollow microcapsules encapsulating rhodamine-labeled dextran were formed by switching the initial placement of the polyelectrolytes in the two phases of the ATPS (e.g., FIG. 4D). In both cases, there is a slightly higher rhodamine signal around the interface of the capsule, indicating some dextran, likely entangled, is in the shell/film. The localization of PSS in the microcapsule shells/films was also confirmed by the strong fluorescence signal resulting from fluorescently labeled PSS ("f-PSS") in the shell/film (FIGS. 4C-4D). Interestingly, it was determined that PSS was always present in the interior of the capsules regardless of its initial placement. This result also suggests that PSS is able to diffuse through the shell/film during complexation and that the shell/film composition is likely to be uniform throughout its thickness.

Figure 5A:
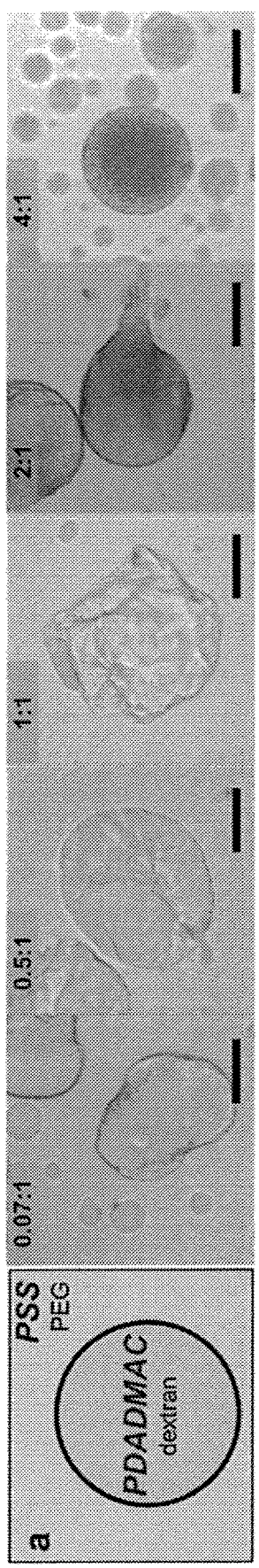
FIGS. 5A and 5B are complexes formed by complexation of two electrolytes at different molar charge ratios in accordance with aspects of the invention.
Figure 5B:
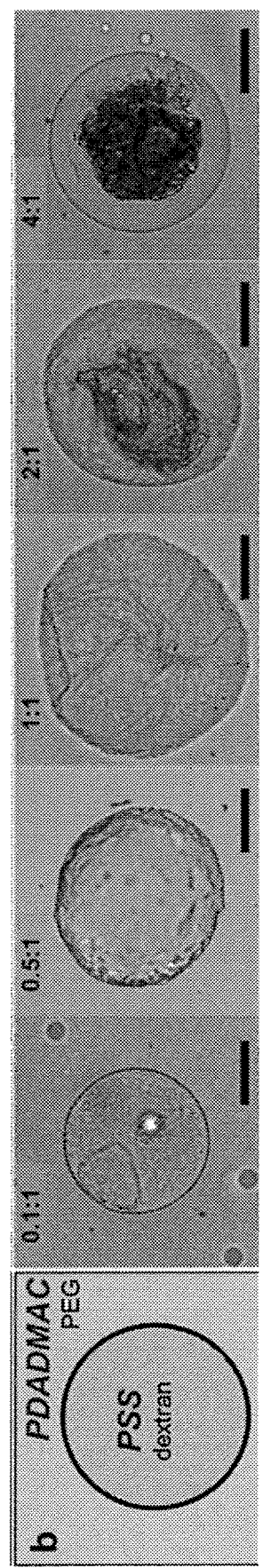

To test the flux-dependent complexation hypothesis at this smaller, submillimeter scale, the charge ratio of PSS/PDADMAC is again varied but over a greater range. Capsule formation was studied with PDADMAC fixed at 0.5% in the dextran phase and PSS at concentrations from 0.01 to 2.56% in the external PEG phase, corresponding to molar charge ratios of 0.05:1 to 4:1. As shown in FIG. 5A, when the charge ratio of PSS/PDADMAC is 0.07:1, the dextran droplet is not completely contained, as evidenced by the satellite drops and nonuniformity of the interface complex. This droplet represents the case in which the PDADMAC flux is too rapid, allowing complexation to occur just outside the droplet interface. For molar charge ratios of 0.5:1 and 1:1, the fluxes are balanced so that complexation occurs near the interface, resulting in wrinkled microcapsules. As shown in FIG. 4B, these wrinkles can be removed by osmotically swelling the capsules. Increasing the PSS concentration further to ratios of 2:1 and 4:1 again creates imbalanced fluxes, but the imbalance this time allows PSS to enter the droplet and complex with PDADMAC in the internal drop space, resulting in a loosely complexed drop (2:1) and a coacervate structure within the droplet (4:1). Similar trends were observed if the initial placement of the polyelectrolytes is reversed (FIG. 5B), supporting the importance of mass transport in determining the location of complexation and the need to tune the fluxes to form complex films at the interface of the ATPS. Both microcapsules and microgel particles can be created with the same four components, e.g., the higher affinity of PSS toward the dextran Phase may produce microgel particles when PSS is originally in the dextran phase and may produce microcapsules when PSS is introduced from the PEG phase.

Figure 6A:
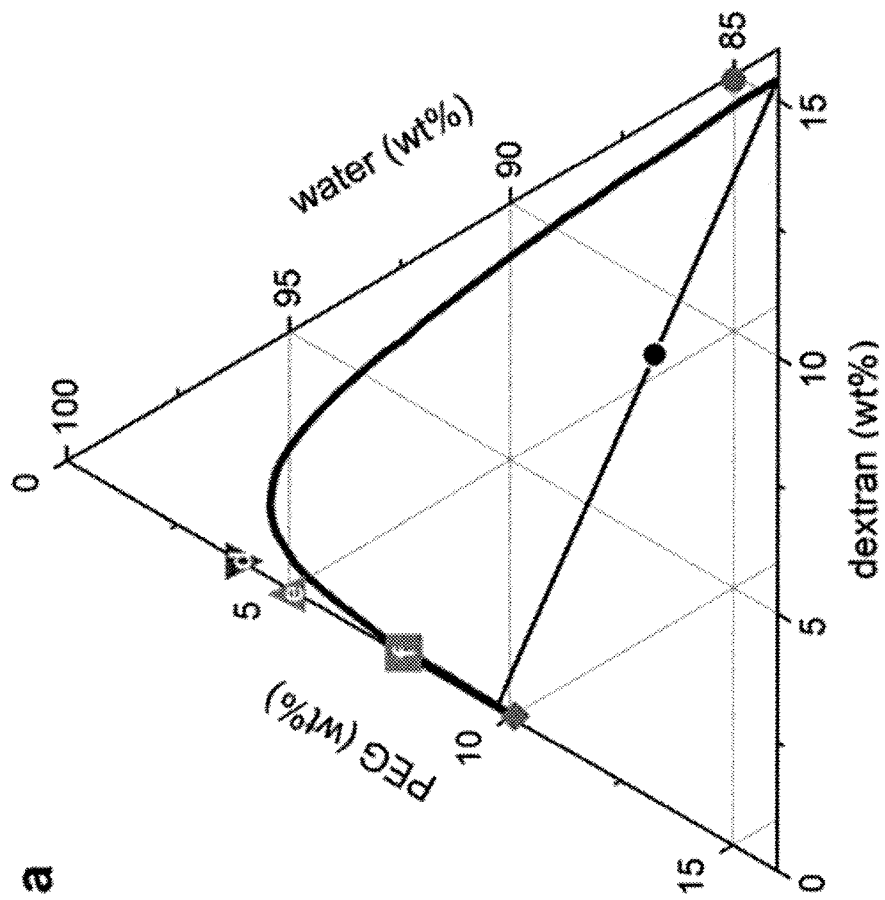
FIG. 6A is a ternary phase diagram with a binodal line for PEG having a molecular weight of 20,000 and dextran having a molecular weight of 500,000 in water according to aspects of the invention.
Figure 6B:
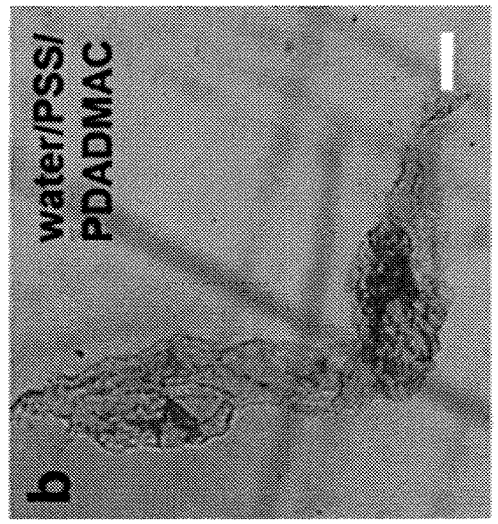
FIGS. 6B and 6C are images of microcapsules having films formed of varying amounts of two oppositely charged components in accordance with aspects of the invention.
Figure 6C:
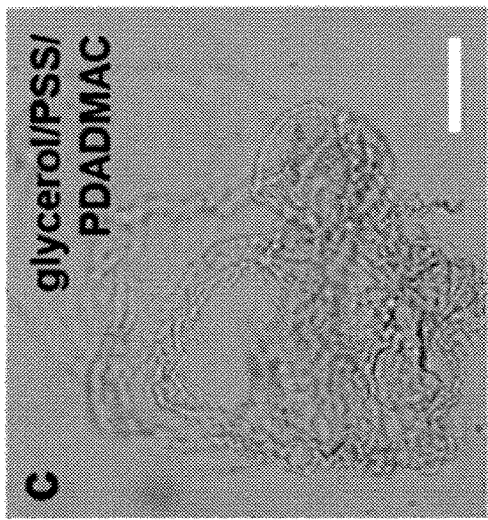
Figures 6D, 6E, 6F:
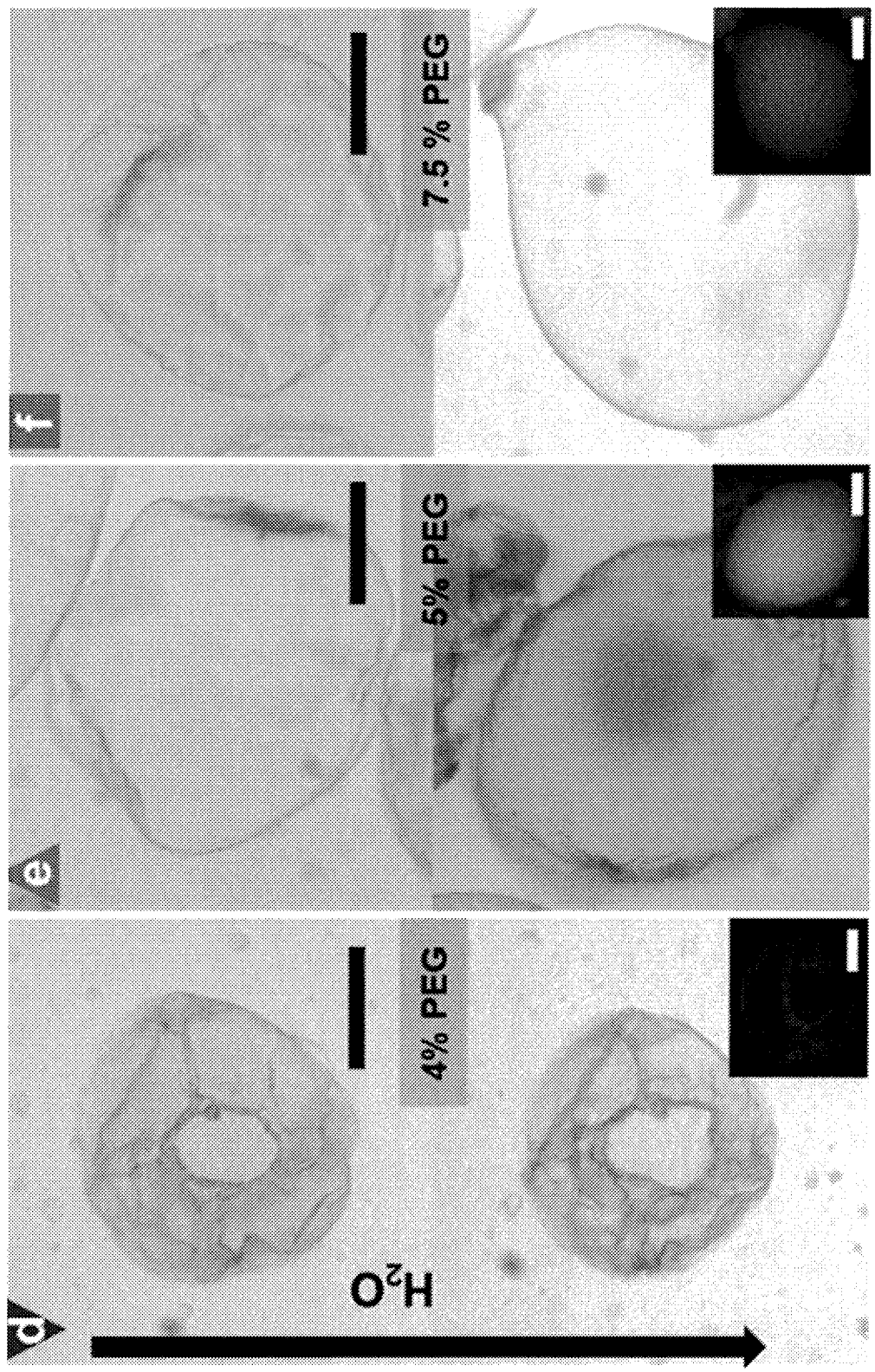
FIGS. 6D-6F are images of microcapsules having films formed of varying amounts of two oppositely charged electrolytes as imaged in PEG in the top row and imaged in pure water in the bottom row according to aspects of the invention.

To test whether proper balancing of the fluxes of the two polyelectrolytes could allow complexation and capsule formation in the absence of an interface an aqueous solution of PDADMAC without PEG or dextran was electrosprayed into an aqueous solution of PSS (FIG. 6B). In this case, capsules were not observed but rather elongated complexes that may bear structures related to the impingement of a jet as the miscible droplet contacted the bath surface. To mimic the viscosities of the original PEG and dextran phases in a miscible system, glycerol is added to the PDADMAC solution, which was electrosprayed into the glycerol and PSS solution. Again, coacervates are formed, but no encapsulating membranes are observed. These experiments suggest that finite interfacial tension plays an important role in capsule formation. These studies suggest that together, finite tension and high internal phase viscosity allow the drop to persist over time scales that allow the complexation to occur without loss of drop integrity. As such, interfacial tension is a key component to maintaining the droplet interface for templating complexation.

To gain further insight into the effect of the interfacial tension and at the same time to balance the osmotic pressures of the two phases, the continuous PEG phase concentration was varied. In an ATPS in equilibrium, as the compositions of the two phases move closer to the critical point, the interfacial tension decreases. Likewise, by decreasing the concentration of PEG in the continuous phase, it was expected that the interfacial tension between the two aqueous phases to decrease. These variations in the PEG concentration are shown on the phase diagram in FIG. 6A. As the continuous PEG phase concentration is decreased down to 5%, the resulting structures show less wrinkles and appear more inflated than those prepared with a 10% PEG solution, as expected due to the lower continuous phase osmotic pressure. However, below 5% PEG, intact capsules are no longer observed, as the RD70 is no longer detected (fluorescence inset). This effect is likely due to the diminishing interfacial tension, which may alter the hydrodynamics as the drops are formed and impedes the formation of encapsulating shell/film via complexation of PDADMAC and PSS. These observations indicate that the interfacial tension of the ATPS, albeit small, is necessary for templating the formation of microcapsules via complexation.

Example 2—Stimuli-Responsive Properties of the Microcapsules

Figures 7A, 7B:
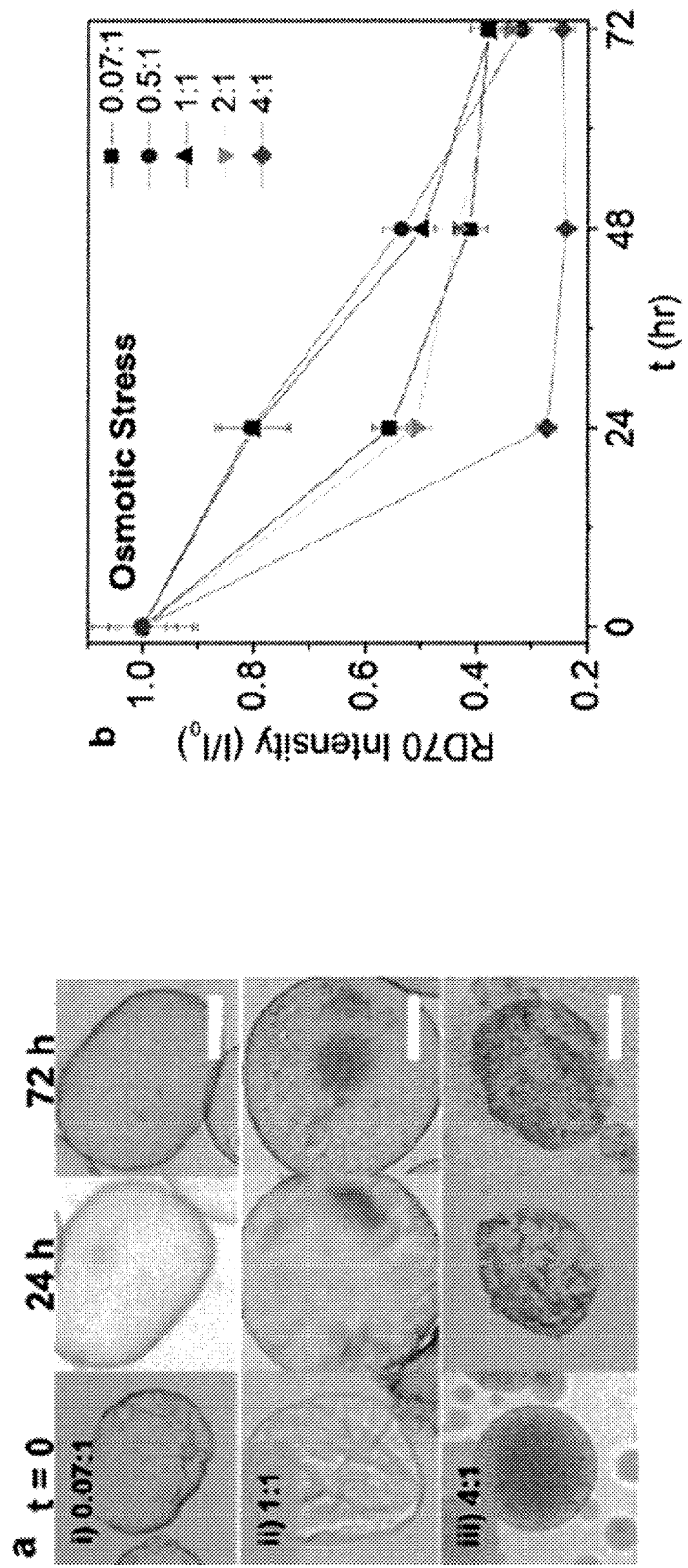
FIG. 7A is an image of microcapsules having films formed with varying amounts of poly(sodium 4-styrenesulfonate) in a PEG continuous phase in accordance with aspects of the invention.
FIG. 7B is a graph illustrating the measured intensity loss of RD70 dye over time due to net negative osmotic stress according to aspects of the invention.
Figure 7D:
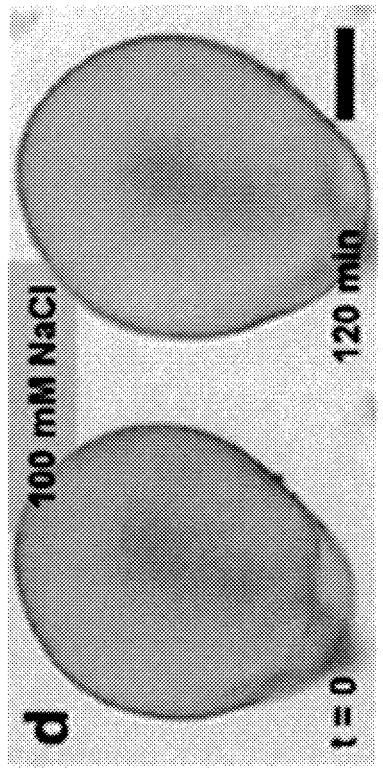
FIG. 7D is an image of microcapsules having a 0.5:1 ratio of electrolytes dialyzed in water according to aspects of the invention.
Figure 7E:
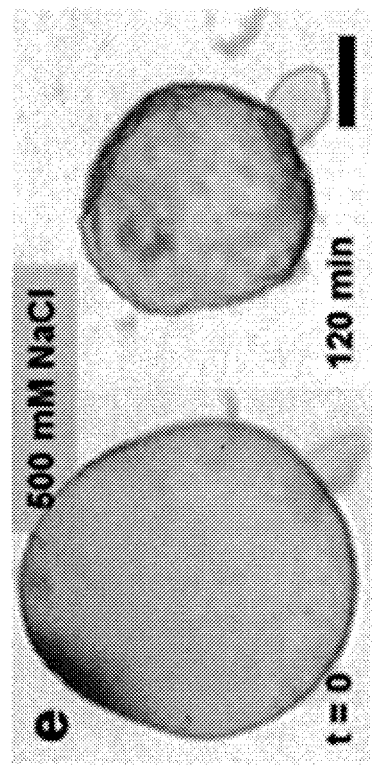
FIG. 7E is an image of microcapsules of FIG. 7D after introducing 500 mM NaCl.

Polyelectrolyte microcapsules undergo drastic changes in their permeability and/or shape when the ionic strength or osmotic pressure of the solution is changed. To test these properties, the coacervates and capsules presented in FIG. 5A were both osmotically and ionically stressed and monitored over time. To monitor the release of encapsulated materials, 1 mg/mL RD70 is mixed in 15% dextran along with 0.5% PDADMAC and electrosprayed into the corresponding molar charge ratio PSS and 10% PEG continuous solutions. The resulting structures were dialyzed against pure water, which subjects the capsules and coacervates to a net negative osmotic pressure, resulting in their expansion. Over time, the capsules with 0.07:1 and 1:1 ratios of the two polyelectrolytes retained their shape, while the 4:1 coacervate droplets lost their integrity and began to disassemble as shown in FIG. 7A. After 24 hours of net negative osmotic stress, 0.5:1 and 1:1 capsules retain 80% of the original dye, 0.07:1 and 2:1 capsules retained only 50%, and the 4:1 coacervate droplets have released all encapsulated dye. Different abilities to encapsulate dextran molecules are consistent with the visual trend observed in FIGS. 3A-3D and FIGS. 5A and 5B in which there appears to be a structural optimum based on fabrication conditions. The microcapsules that were created with 0.5:1 and 1:1 charge ratios were more mechanically resilient than ones made with 0.07:1 and 2:1 in their ability to retain encapsulated cargo because the capsules were formed while the fluxes of the two polyelectrolytes are delicately balanced.

Figure 7C:
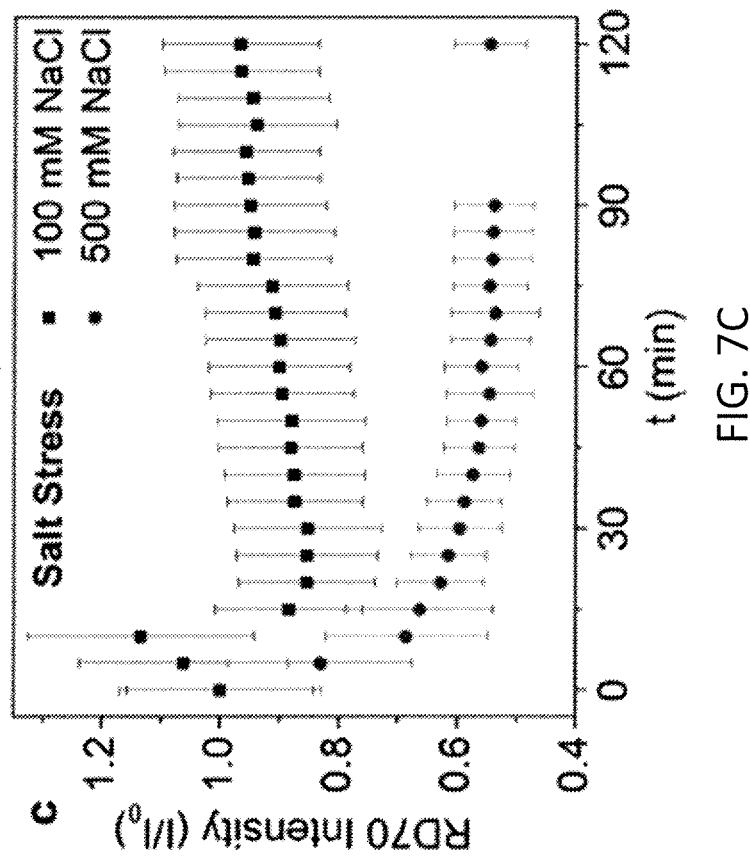
FIG. 7C is a graph illustrated the standard error of average intensities of at least 8 capsules in response to salt stress per time point in accordance with aspects of the invention.

The response of the microcapsules to changes in the ionic strength was tested by exposing capsules made under 0.5 PSS:1 PDADMAC charge ratio to 100 mM and 500 mM NaCl. RD70 was encapsulated in the lumen of the capsule to enable monitoring of the triggered release. While little changes in the shape and fluorescence intensity are observed in the case of 100 mM NaCl treatment, significant release of the RD70 as well as shrinkage of microcapsules are observed within 60 min for the higher salt concentration, e.g., FIG. 7C. The shrinkage and release of the encapsulated dye suggested that an increase in the ionic strength induces change in the permeability of the microcapsule shell/film through dissociation of polyelectrolyte complexes. These results confirm that polyelectrolyte microcapsules and coacervates formed via complexation in ATPS indeed exhibit stimulus-responsive properties and imply that microcapsules that respond to different stimuli such as pH or temperature can potentially be assembled using different types of polymers.

Example 3—Encapsulation of Live Bacteria

One of the most significant advantages of the ATPS is its inherent biocompatibility. Nanocultures, semipermeable microcapsules with internal volume of nanoliters, were developed for use in sequestering and interrogating microbes and their microcolonies in contact with growth media, antibiotics, and in interaction with other kingdoms. Encapsulation of living cells in a stable ATPS, in particular, could offer unique opportunities by maintaining cell viability and at the same time interrogating cells by diffusing analytical probes from the continuous phase.

Figures 8A, 8B:
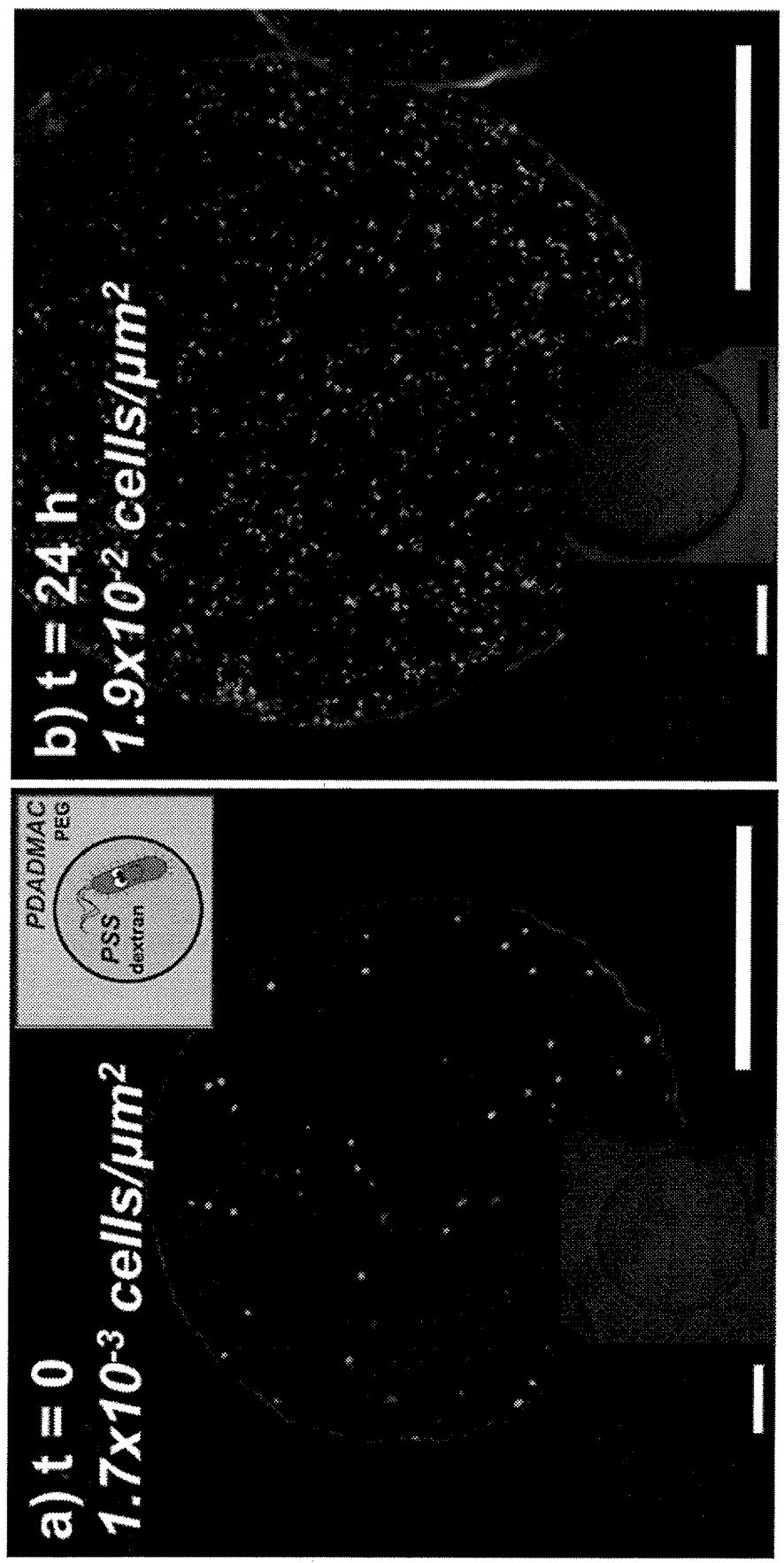
FIGS. 8A and 8B are images of microcapsules encapsulating living cells, shown in green, and dead cells, shown in red, in accordance with aspects of the invention.

Accordingly, bacteria were encapsulated within the polyelectrolyte capsules made under a 1:1 charge ratio of PDADAMAC and PSS to create all aqueous nanocultures, i.e., all aqueous nanoliter-scale compartments that can host microbial cells. To create these capsules, the droplet phase of 15% dextran and 0.64% PSS was mixed with 20 µL/mL stationary phase *Pseudomonas aeruginosa* (PAO1; OD 0.02) and a mixture of glycerol and vitamins. The continuous phase consisted of 10% PEG and 0.5% PDADMAC. Upon the formation, the bacteria-containing capsules were moved to a continuous phase consisting of 15% dextran with the glycerol and vitamins to maintain a consistent media environment and incubated at 37° C. Initially after loading or after 24 hours, the capsules were exposed to a Live/Dead staining assay and imaged under a confocal microscope as shown in FIGS. 8A-8B. By comparing the total number of cells (live and dead, green signal) within the pictured area, there is an order of magnitude increase in total cells/µm2 from $1.7 \times 10^{-3}$ at t=0 to $1.9 \times 10^{-2}$ at t=24 h, indicating that the scarce-nutrient polyelectrolyte microcapsules enable cell growth and the viability of the cell can be probed by taking advantage of the permeability of the shell/film. Control growth studies indicate that PSS slightly retards the growth of the PAO1 but does allow proliferation, as seen in FIGS. 8A-8B.

The flexibility to choose the placement of the two polyelectrolytes in the two aqueous phases was extremely useful because PDADMAC is known to display antimicrobial properties. By simply switching the initial location of the PDADMAC to the drop phase and performing the cell encapsulation experiment described above, it was confirmed that no cell growth occurs. Thus, by placing the PDADMAC in the continuous phase, microbes are viable, whereas if it is in the drop phase, the microbes in the nanocultures are not. The latter configuration could be useful in encapsulation applications that require sterile conditions.

Example 4—Aqueous Two Phase System Using Nanoparticles to Produce a Microcapsule Having a Compartment A new technique for the spontaneous fabrication of all-aqueous double emulsions is provided in this Example.

The aqueous two phase system of poly(ethylene glycol) ("PEG") and dextran was used to create an interface in which anionic silica nanoparticles ("NPs") and a cationic polyelectrolyte ("PE") were included in the phases, respectively. An osmotic pressure imbalance existed between the two phases, which lead to the spontaneous formation of the double emulsion. The size of the inner PEG drop was determined to be a function of the initial concentration of silica. As the silica concentration is increased, the inner PEG drop size decreased. Interestingly, even after this initial fabrication step, PEG was still able to slowly penetrate the shell/film and exchange with the inner drop. The shell/film was also readily permeable to small molecules, which could partition to either the dextran or PEG phase within the capsule. A simple reaction was carried out to show how reactants may be delivered to the core to carry out more complicated functions.

To produce the all-aqueous double emulsions, dextran-rich phase containing positively charged PE, poly(diallyldimethylammonium chloride) (PDADMAC) were electrosprayed into a PEG-rich phase with 22 nm $SiO_2$ nanoparticles (NPs). The concentrations of NPs and PDADMAC in the two phases are adjusted such that a wrinkly skin is formed, indicating interfacial complexation.

Unexpectedly, what appears to be microcapsules with internal droplets were observed. However, the aqueous double emulsions were distinctly different from the double emulsions in the above examples using a film formed of two oppositely charged electrolytes as the outer interface clearly showed the presence of a rigid shells/films. In contrast, the internal droplets look like droplets dispersed in an immiscible liquid. Another interesting observation is that the size of internal droplets decreases with an increase in the concentration of 22 nm NPs in the PEG phase, as seen in FIG. 9A-9C.

To confirm the compositions of the two internal phases within the microcapsules and observe the physical location of nanoparticles, the PEG, dextran, and NPs were fluorescently labeled (e.g., see FIG. 1d). These results confirmed that the included droplet was PEG, the continuous droplet phase was dextran, and the NPs did not leave the interface, so that the inner droplet interface is that of PEG-dextran.

To understand the mechanism behind the formation of internal droplets and verify that double emulsion formation is not a result of the spraying process, the pendant drop method was used. The pendant drop method enables direct visualization of morphology evolution without high shear. In this case, 0.5 µL of a solution of 15% dextran and 0.25% PDAMDAC was injected into solutions of 10% PEG and two concentrations of 22 nm diameter NP, FIG. 2. Without complexing agents, injecting the dextran drop into the continuous PEG resulted in instant detachment due to the ultra-low interfacial tension between the two phases. However, when NPs were initially included in the PEG phase, as depicted in FIG. 9A, the final structure was a dextran drop stabilized with a NP-PDADMAC membrane that ultimately includes distinct PEG drops, as seen in FIG. 9D. The amount of included PEG in the dextran phase was contingent upon the concentration of NPs in the continuous PEG phase. At 2% NP, illustrated in FIG. 9B, there are large PEG drops that nucleate from the NP-PDADMAC membrane that ultimately dewet and migrate upwards due to their buoyancy. Doubling the NP concentration, FIG. 9C, results in smaller drops nucleated along the membrane that similarly dewet and float towards the needle.

Figures 11A, 11B, 11C:
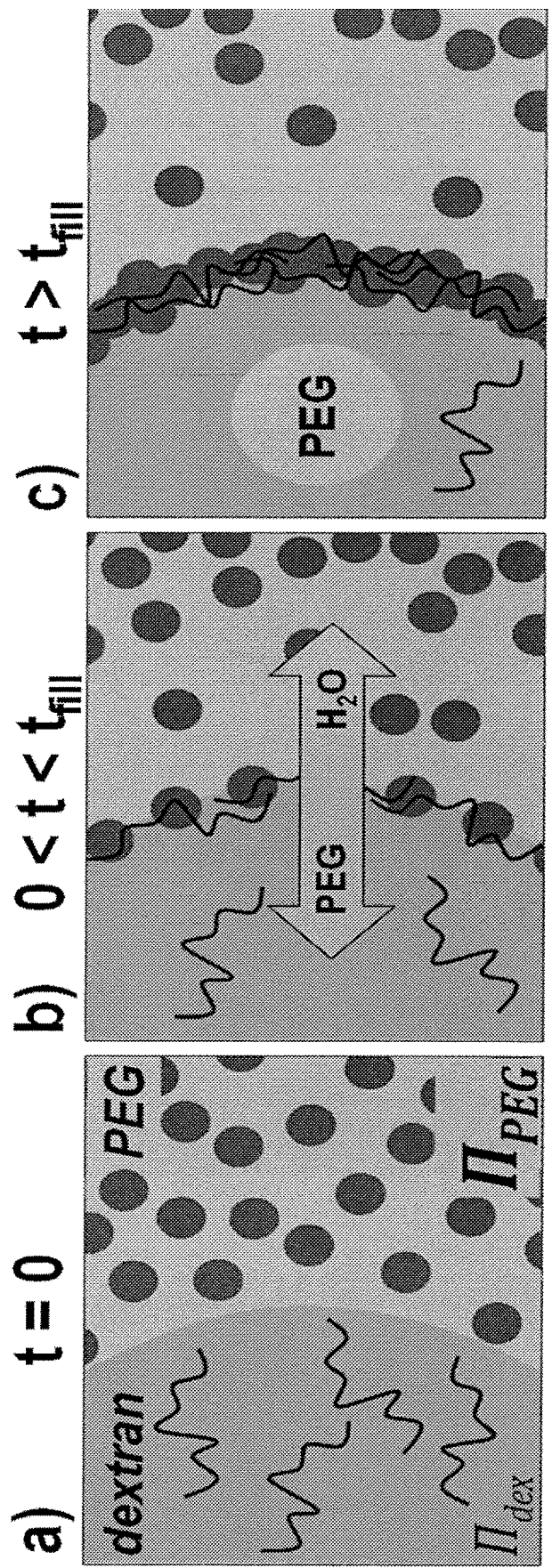
FIGS. 11A-11C are schematics illustrating the location of charged nanoparticles and charged electrolytes at the initial time of injection, during a period between the initial time of injection and the filling of the film's pores, and at the time the film's pores are filled, respectively, in accordance with aspects the invention.

At the initial introduction of dex/PDADMAC to PEG/NP at t=0, a clean interface exists across which there is an osmotic pressure imbalance ($\Pi_{PEG}>\Pi_{dex}$). Next, when the first NPs attach to the interface and begin to complex with the PDADMAC fluxing out of the dextran phase, the initial complex is rigid due to the incorporation of NPs but porous due to their distinct size. Note, the NP have a near complete affinity for the PEG phase and therefore do not flux into the dextran phase. Therefore, to balance the osmotic pressure, water from the dextran droplet is displaced by PEG, which is devoid of NP, from the continuous phase. This exchange continues until enough NPs are included in the membrane and the pores are 'filled', at some time, till. This proposed mechanism is presented schematically in FIG. 11A-11C.

To test the proposed mechanism, microcapsules with SiO$_2$ NPs of two different sizes were generated and the effect of NP concentrations on the size of internal droplets was studied. A lower concentration of 8 nm NPs were required to achieve the same fraction of included PEG, which was consistent with an increase in number density of smaller NPs. However, this volumetric factor alone was not enough to describe the difference in included PEG, since by shifting the 22 nm NP curve by a factor of 20 does not collapse the curves. In addition to changing the number of particles at a given concentration NPs for different sizes, the diffusive transport and osmotic driving forces are also affected, complicating the non-dimensionalization of the data. Despite this challenge, these data are meaningful in describing the trend of predictably manufacturing double emulsion microcapsules; although higher NP concentrations induce a larger osmotic pressure imbalance, $t_{fill}$ is lower, leading to a quicker filling of the pores, and resulting in smaller drops, e.g., as seen in FIGS. 10B-10C.

The final structure of the injected droplet was dependent on the initial placement of the charged moieties. The final microcapsules were shelled-w/w/w double emulsions, which could be utilized as biologic compartments, either as micro reactors or model protocells, potentially requires both large and small molecules to transport across the membrane.

Figure 11D:
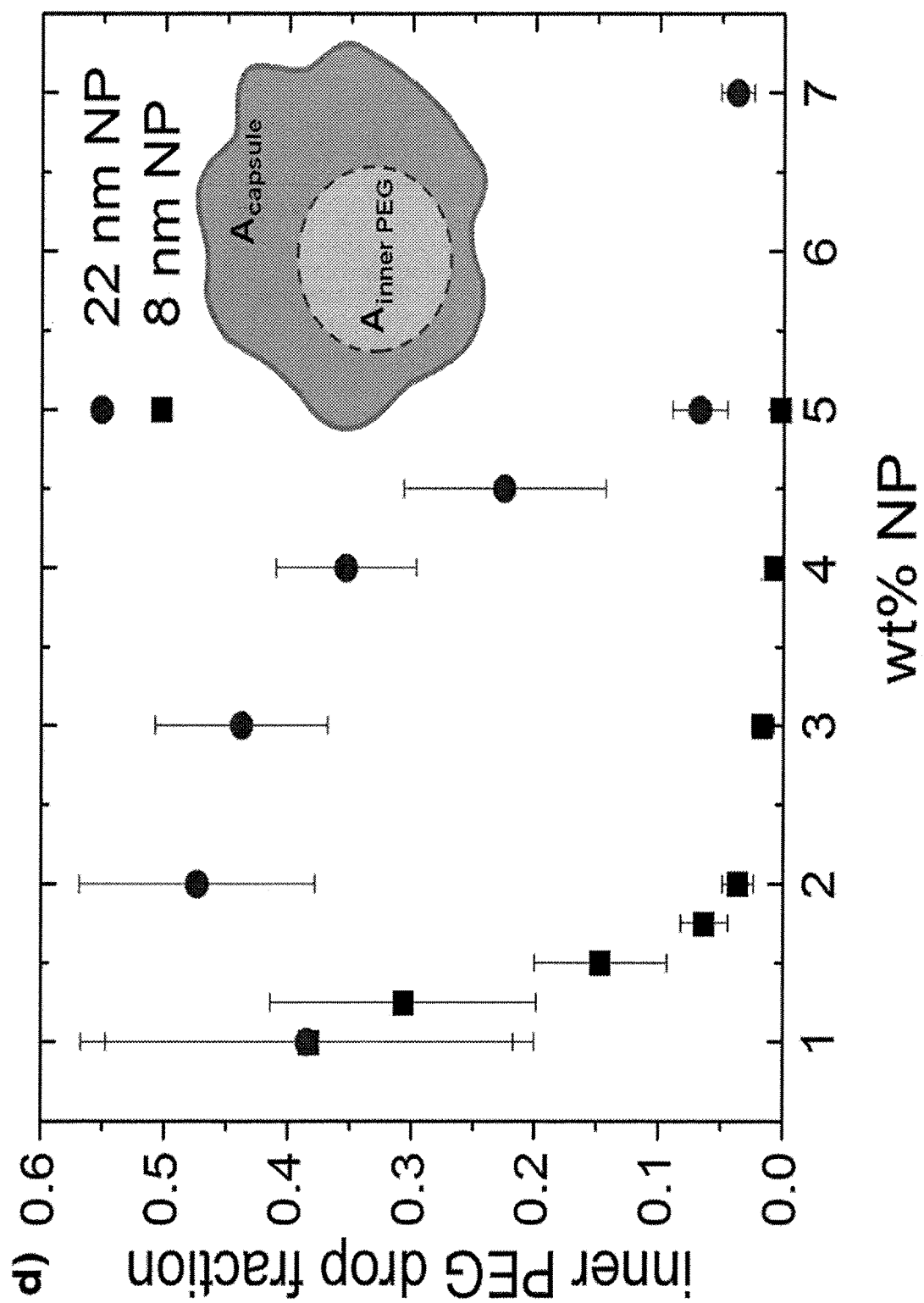
FIG. 11D is a graph of included PEG drop normalized by the capsule area as a function of nanoparticle concentration in the PEG phase according to aspects of the invention.
Figure 12A:
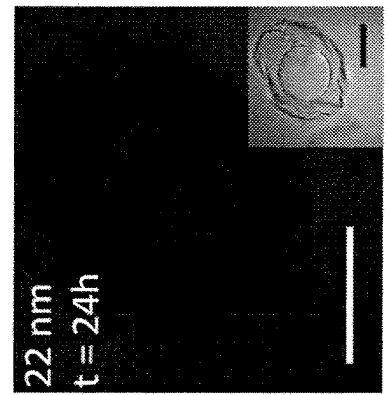
FIG. 12A is a schematic of a measurement geometry for a microcapsule in accordance with aspects of the invention.
Figure 12B:
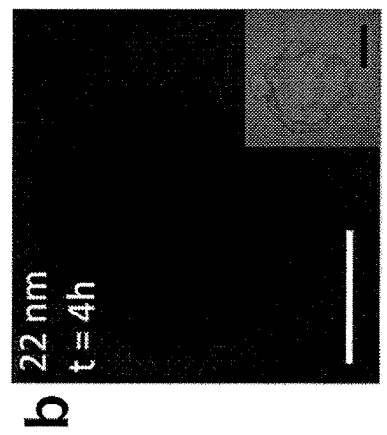
FIGS. 12B and 12C are images of a microcapsule measured four hours and eight hours after the addition of f-PEG, respectively, according to aspects of the invention
Figure 12C:
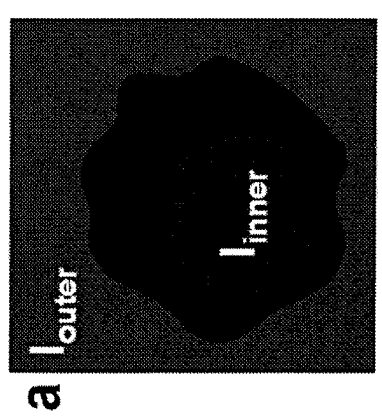
Figure 12D:
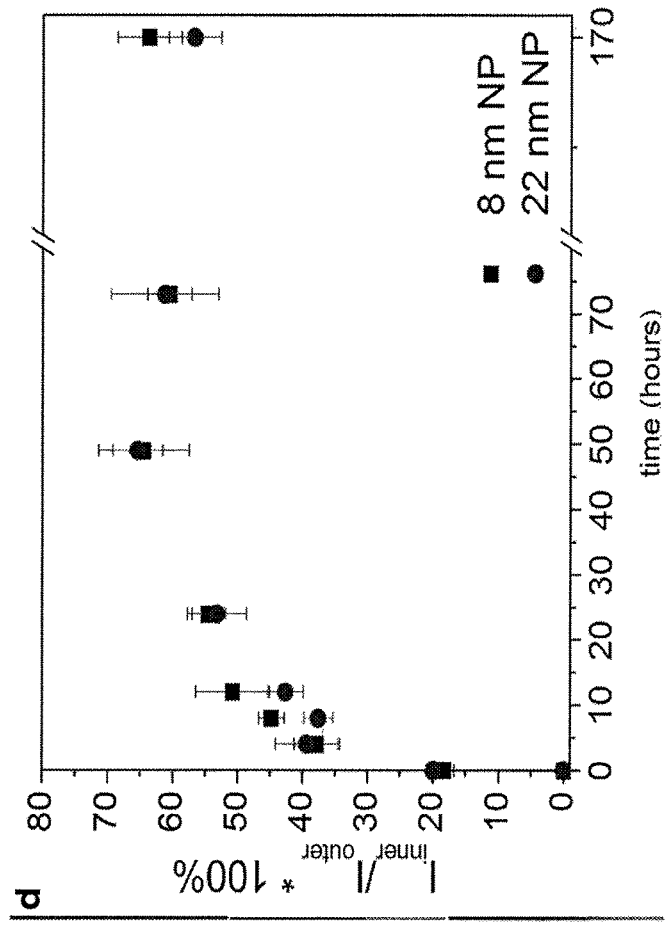
FIG. 12D is a graph the concentration of f-PEG in the inner PEG drop as a function of time for microcapsules made with both 8 nm and 22 nm nanoparticles in accordance with aspects of the invention.

To test shell/film permeability within the microcapsules, f-PEG was added to the outside and the intensity inside the capsule was measured. Interestingly, there was an exchange of f-PEG with the inner PEG drop, as seen FIGS. 12A-12D. To generate these data, f-PEG was added to achieve a concentration of 0.5 mg/mL in solutions of 1.33% 8 nm SiO$_2$ and 4.5% 22 nm SiO$_2$ capsules. These capsules have approximately the same inner PEG drop size, as shown in FIG. 11D. FIG. 12A schematically shows the intensities measured and FIG. 12B-12C are representative images of the 22 nm NP capsules. As seen in FIG. 12D, both size NP capsules had the same permeation behavior over time. The intensity fraction only reached 65%, even after one week. This equilibration value w a function of the initial concentration of f-PEG added, and does not depend on the inner PEG drop fraction. The implication of this slow exchange of PEG suggests there are two dynamic time scales which are in play within this system. First, $t_{fill}$ determines the initial size of the included PEG drop. This time is very small as it happens nearly instantly during microcapsule fabrication. Then, PEG-like molecules continue exchanging with the inner PEG drop on much longer time scales. The slow exchange of these larger molecules allows staged introduction of different materials at different time scales.

Figures 13A, 13B:
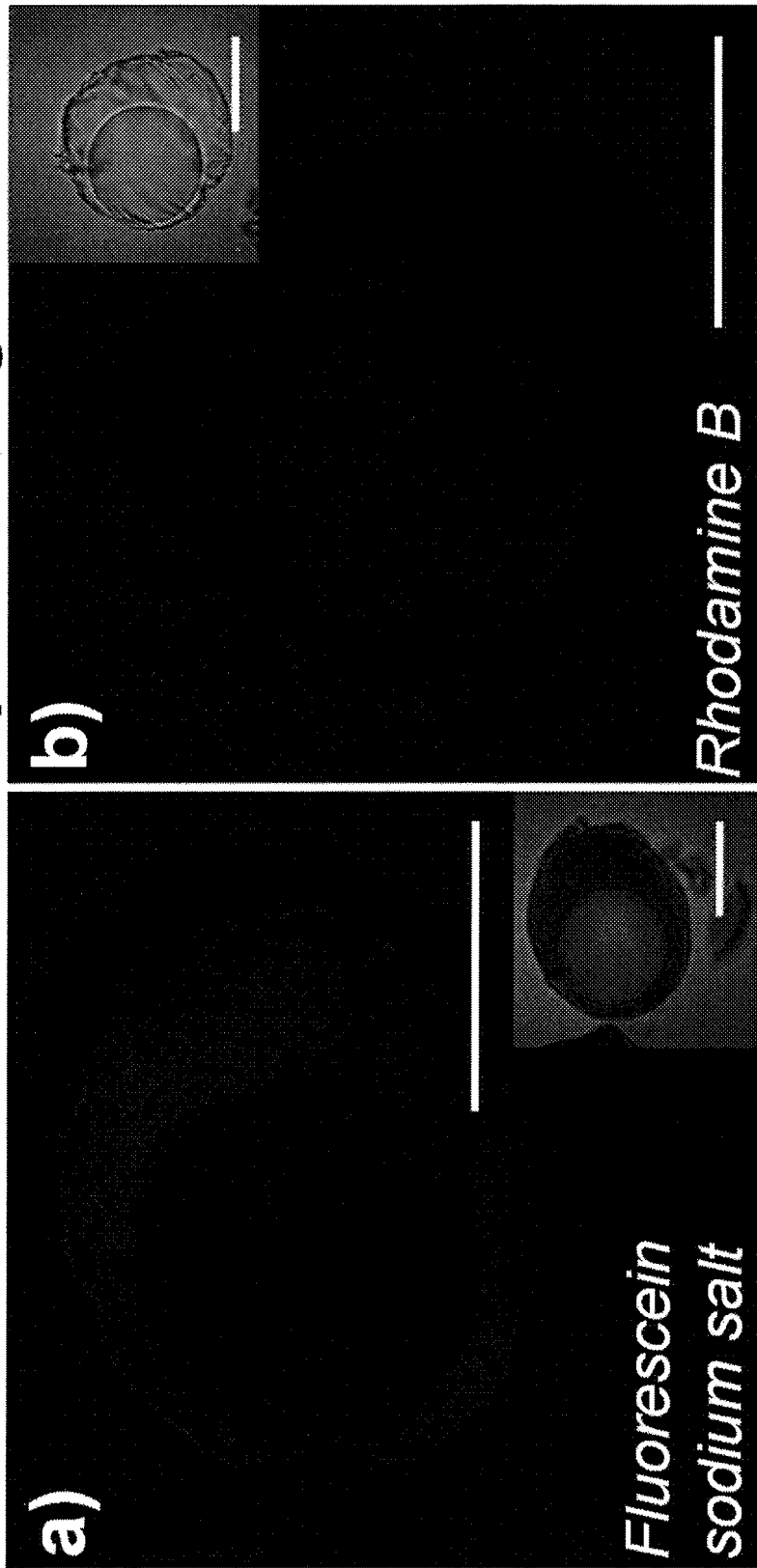
FIG. 13A is an image of a microcapsule with fluorescein sodium salt located predominantly in the dextran phase according to aspects of the invention.
FIG. 13B is an image of is Rhodamine B located predominantly in PEG phase according with aspects of the invention.

Compared to the larger PEG, small molecules, including Fluorescein salt and Rhodamine B, penetrated the shell/film instantly allowing for quick delivery, as seen FIGS. 13A-13B. Interestingly, these two small molecules also partition to the dextran and PEG inner phases, respectively.

Figure 13C:
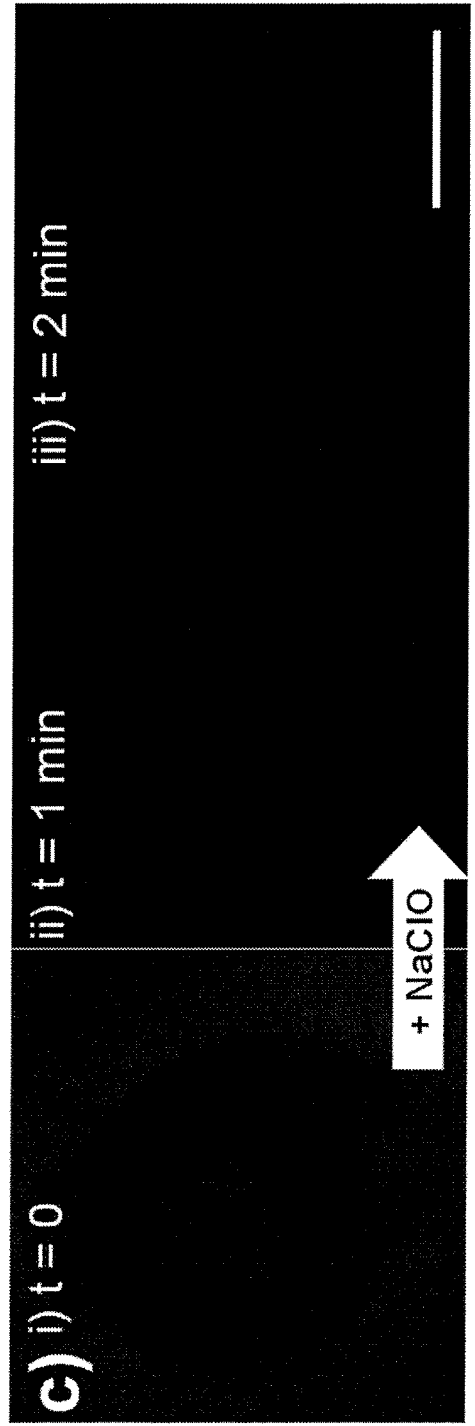
FIG. 13C is an image of a microcapsule with NaClO (bleach) added to the outer PEG phase in accordance with aspects of the invention.
Figure 13D:
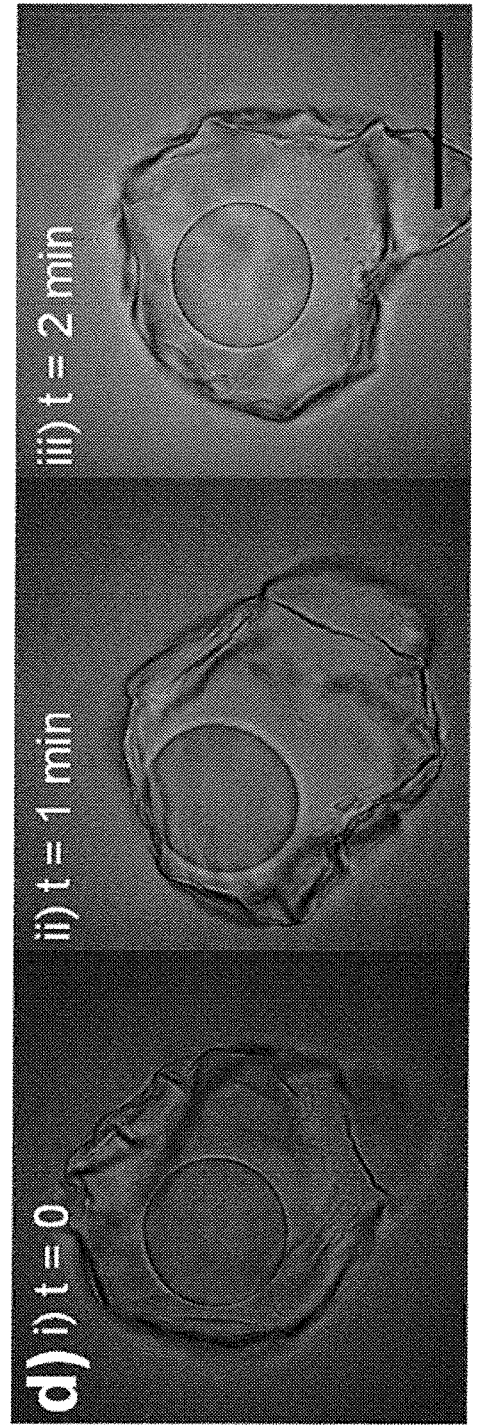
FIG. 13D is a bright field image of the image of FIG. 13C.

Reactive components may also be introduced by way of initial inclusion in continuous PEG phase. Because of the permeable membrane, the reactive components may then permeate into other phases. One powerful implementation of this ability is to couple the natural chemical partitioning of one reactive component and introduce a second reactive component from the continuous PEG phase. A simple demonstration of this reaction was the quenching reaction of f-PEG, as seen FIGS. 13C-13D. Microcapsules were fabricated with f-PEG and sodium hypochlorite (bleach) was introduced from the outer phase. The product of this simple reaction is the extinction of the fluorescent signal. This product is seen quickly, as shown by the lack of fluorescent signal in FIG. 13C, after only 2 minutes of diffusion. Additionally, biologic functionality may be imparted on the shell/film by including an additional charged moiety. For example, lysozyme may be included in the shell/film by initial mixing in the dextran phase, after which it would complex with the NP at the interface, along with PDADMAC.

The capsules were capable of dismantling/disruption by the adjustment of the pH to less than 5. At this point, the silica and PDADMAC become less adhesive. These capsules are very tolerant to high salt concentration, requiring more than 1 M NaCl to break apart the shell/film. High salt tolerance is another benefit over the polyelectrolyte microcapsules for biologic microenvironment tests, which are often carried out in buffers.

This spontaneous, yet controllable fabrication method, along with the ease of impregnation with alternative materials, as in the case of lysozyme, makes this technique a valuable method for functional, biocompatible and biomimetic structures. A weak polyelectrolyte may be substituted to strengthen the pH response or the shell/film may be doped with reactive catalytic nanoparticles to create the framework for microreactor capsules—thus, the possibilities for including different materials are numerous.

Example 5—Aqueous Two Phase System Using Nanoparticles to Produce a Microcapsule without a Compartment In this Example, microcapsules were formed by injecting a dextran composition having NPs into the a PEG phase having charged electrolytes. Unlike the microcapsules produced in Example 4, these structures were not double emulsions, although they do follow the same mechanistic driving force, in the opposite direction.

ATPS with two microcapsules were formed using charged electrolytes and nanoparticles were produced. Poly(ethylene glycol) (PEG, MW=20 000 g/mol), dextran from *Leuconostoc* spp. (MW=450 000-600 000 g/mol), poly(diallyldimethylammonium chloride) (PDADMAC, 20 wt % MW=200 000-350 000 g/mol), LUDOX® TM-50 colloidal silica (22 nm diameter, 50 wt % suspension in water), LUDOX® SM colloidal silica (8 nm diameter, 30 wt % suspension in water), rhodamine B (≥95%, HPLC grade), fluorescein sodium salt, tetramethylrhodamine isothiocyanate mixed isomers (TRITC), 3-aminopropyl)triethoxysilane (APTS), and tetraethyl orthosilicate (TEOS) were purchased from Sigma-Aldrich™. Rhodamine B-tagged dextran (f-dex, MW=70 000 g/mol), sodium hypochlorite (bleach, 8.25% solution), ammonia, and ethanol (200 proof) were purchased from ThermoFisher Scientific™. Rhodamine-tagged PEG (f-PEG, MW=20 000 g/mol) was purchased from Creative PEGWorks. Fluorescent silica nanoparticles (f-NP, 18 nm diameter) were synthesized. Briefly, 2 mg TRITC was mixed with APTS at a 50:1 molar ratio in ethanol and stirred in the dark for 12 hours to make the fluorescent cores. Next, 2 v % TEOS in ethanol was added drop-wise over 20 min. The remaining TEOS was added over 40 min in a solution of ammonia, water, and ethanol and then stirred in the dark overnight to build the silica shell/film. The final concentrations of each component were 0.2 M [$NH_3$], 1.494 M [$H_2O$], and 0.155 M [TEOS] to achieve a nominal particle size of 25 nm. This solution was dialyzed against DI water for 2 days. The f-NPs were imaged with TEM and have an average particle diameter of 18 nm. All chemicals were used as received.

For this example all concentrations expressed in % are wt %. Stock solutions of 20% dextran and 15% PEG were mixed in deionized water and allowed to stir overnight before use in creating droplet and continuous phases, respectively. The dextran droplet phases comprised of 15% dextran and 0.25 or 0.5% PDADMAC were made by measuring the mass of 20% PDADMAC, then 20% dextran, then DI water to achieve the desired concentration. These solutions were vortex mixed and sonicated for at least 2 min each, prior to using. The PEG/silica continuous phases were made by adding 15% PEG by mass, then silica solution by volume, then DI water to achieve the desired concentration. These solutions were vortex mixed and sonicated at least two times each for at least 2 min each time. The pH of the PEG phase was measured to ensure a pH>9.5, else the pH was adjusted with 0.1 M NaOH. The PEG/silica solutions were used within 12 hr of mixing.

Hanging drops of 0.5 μL drops of 15% dextran/2% NPsdrops were injected at a rate of 1 μL/s into a 3 mL cuvette of 10% PEG/PDADMAC. The needle diameter is 0.85 mm in all experiments. Images started recording as the drop was injected. Images were recorded at 1.5 fps.

Microcapsules were fabricated using the same all-aqueous electrospray. The 15% dextran/0.5% PDADMAC phase was injected from a 5 mL syringe at a rate of 500 μL/h, e.g., as discussed above. The glass capillary device had an opening of approximately 150 μm. The voltage drop across the glass capillary device was adjusted between 3000-4000 V to achieve microcapsules of approximate 100-200 μm diameter. The 10% PEG/silica phase was gently stirred at 200 rpm.

When the NPs were initially included in the dextran phase, as depicted in FIG. 14A, the final structure, depicted in FIG. 14D, was a NP-PDADMAC membrane included within the dextran phase. The extent to which the dextran phase is evidently driven out of the membrane is a function of PDADMAC concentration in the PEG phase, as seen in the video snapshots shown in FIG. 14B compared to FIG. 14C. Notably, in FIG. 14C, there is an apparent complexation front that makes its way toward the center of the drop through FIG. 14C until the entire droplet phase makes up a coacervate phase in which NP-PDADMAC is also complexed within the dextran phase. In FIGS. 14A-14D, however, it is $\Pi_{dex}>\Pi_{PEG}$, which flips the sign of the driving force for water. As such, water is driven into the dextran droplet, displacing dextran outside the NP-PDADMAC shell/film.

Figure 15:
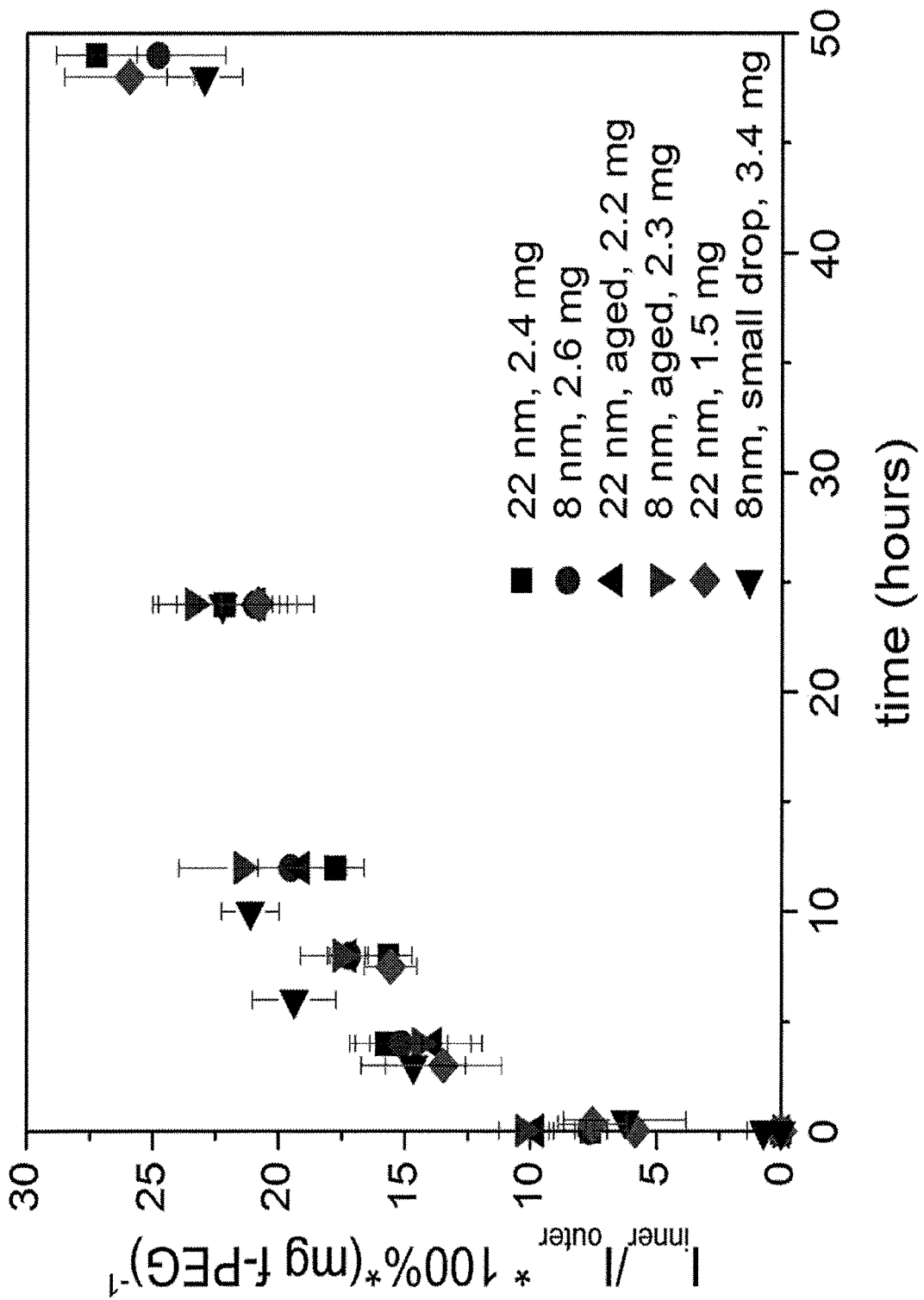
FIG. 15 is a graph of the measurement of PEG permeability into the microcapsules by adding f-PEG to 5 mL continuous PEG phase and normalized by the amount of f-PEG according to aspects of the invention.
Figure 17:
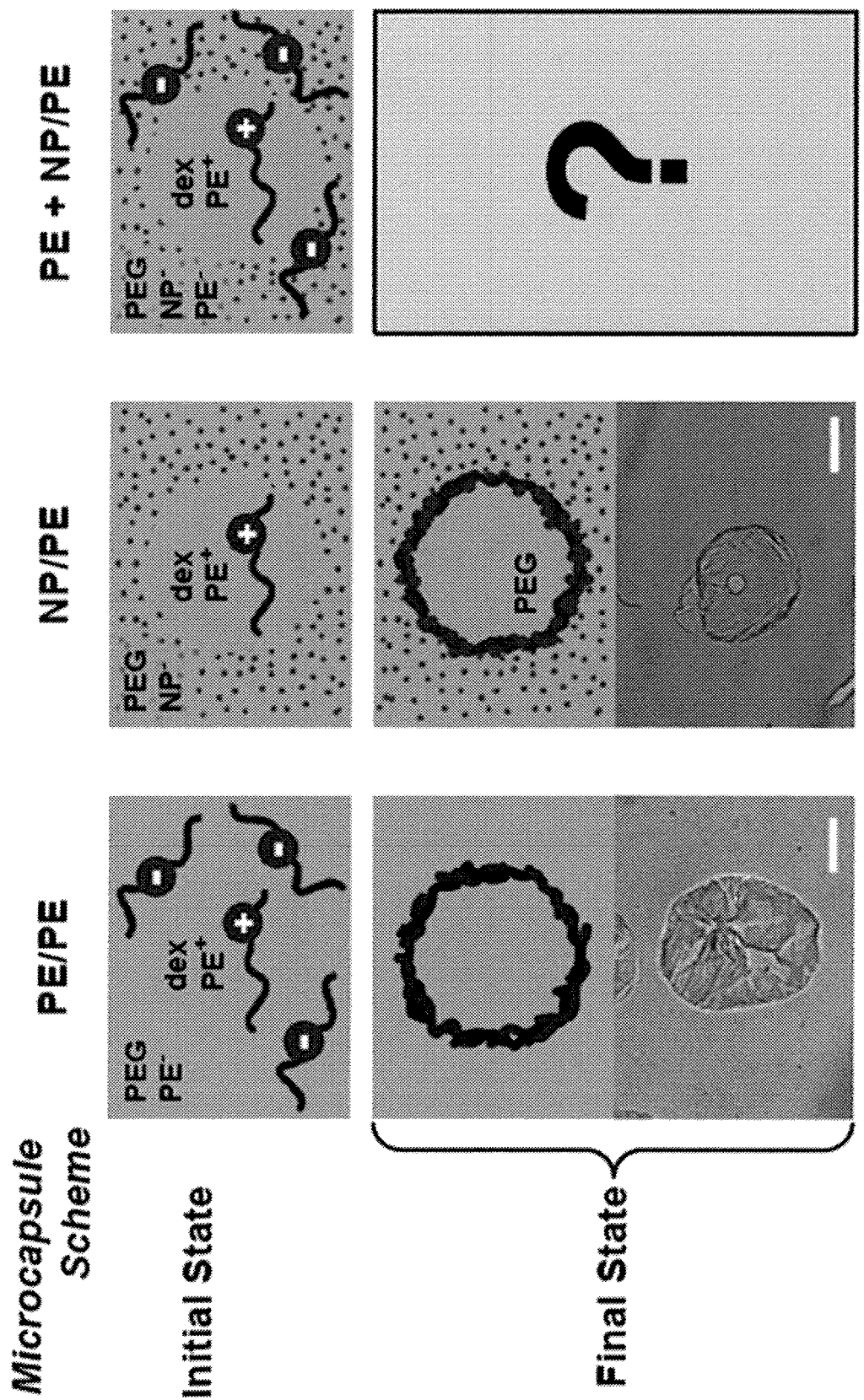
FIG. 17 is a schematic of microcapsules formed in Examples 1-5.

The PEG permeability behavior may also be seen in, e.g., FIGS. 12A-12D, which is consistent for different size fraction PEG drops, different aged capsules, and different NP sizes. Furthermore, the discrete value represented on the y-axis of FIGS. 13A-13D is seen to be a function of the amount of f-PEG added to the solution and can be normalized for all data to fall in the same curve, as seen in FIG. 15. This ability to normalize suggests that the final membrane structure for the example illustrated in FIGS. 12A-13D is similar to this example. FIG. 15 depicts measurements of PEG permeability into pre-made capsules by adding f-PEG to 5 mL continuous PEG phase and normalized by the amount of f-PEG. Legend descriptions indicate the size of silica NP used to fabricate the capsule and the amount of f-PEG added to the 5 mL solution (mg). All capsules were made for inner PEG drop fractions of 0.25 except (◂), which is made to a fraction of 0.05. Data designated as 'aged' (▲, ▽) are capsules that were made 1 week prior to adding f-PEG.

Lysozyme is easily included in the shell/film as it is known to complex with charged silica. Confirmation of this ability is shown in FIGS. 16A-16B, in which the only signal of lysozyme seen in the shell/film. Additionally, due to the strong complexation, phase separation of the lysozyme within the shell/film was not observed. FIGS. 16A-16B illustrate a confocal image of microcapsule fabricated with 15% dextran/0.5% PDADMAC/1 μM rhodamine tagged lysozyme into 10% PEG/4.5% 22 nm silica NPs. Specifically FIG. S3A illustrates a Fluorescent image, where red is the rhodamine tagged lysozyme and FIG. S3B illustrates a corresponding bright field image. Scale bar was 100 μm.

Example 6—Microcapsules Having a Film Formed of Complexation of Polyelectrolytes and Nanoparticles As shown in the above examples, the following general characteristics of microcapsules having a film formed of two charged electrolytes or a charged electrolyte and a charge nanoparticle was determined: encapsulated double emulsions form as a result of rapid association between NPs and polyelectrolytes at the interface, accompanied by osmotically induced transport of external aqueous phase into the interior of the membrane. These encapsulated double emulsions—which may be configured to features that resemble model cells with membraneless organelles—enable hosting and segregating chemically distinct molecules within the lumen, and exchanging materials with the outer phases. However, unlike the microcapsules formed with two oppositely charged polyelectrolytes, which could be stressed without losing structural integrity, these encapsulated double emulsions were extremely rigid, likely due to dense packing of nanoparticles in the shell/film, making them mechanically fragile under osmotic stress and mechanical loading.

Accordingly, in this Example, interfacial membranes were formed in ATPS by introducing cationic polyelectrolyte-containing droplets into continuous baths containing anionic polyelectrolyte and nanoparticles. It is shown that the structure and properties of microcapsules fabricated using this method can be tuned by systematically varying the concentrations of nanoparticles and polyelectrolytes in the outer phase. This tunability, accompanied by the potential for scale-up production, makes ATPS a truly versatile platform to induce the fabrication of functional microcapsules via interfacial complexation for applications in encapsulation, drug delivery, microreaction/separation and controlled release.

Figure 18:
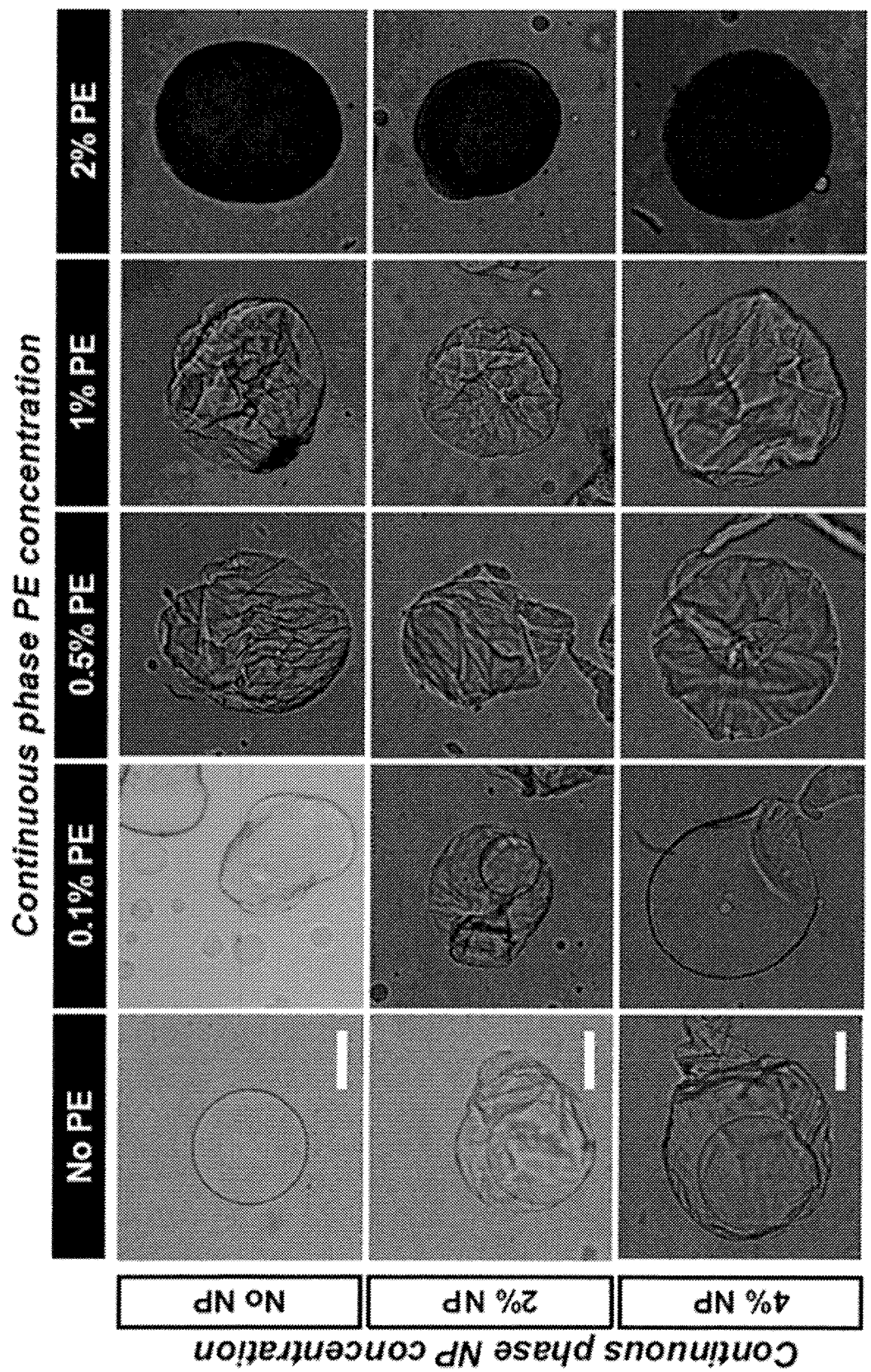
FIG. 18 is an image of microcapsules having various concentrations of charged components.

More specifically, aqueous two phase systems of poly (ethylene glycol) PEG and dextran were used to create the templating interface. Droplets of dextran with a cationic PE, poly(diallyldimethylammonium chloride) (PDADMAC), were dispersed into PEG solutions with anionic 22 nm $SiO_2$ NPs and/or an anionic PE, poly(sodium 4-styrenesulfonate) (PSS), using the all-aqueous electrospray method. To illustrate the effect of NP and PSS, the concentration of PDADMAC in the dextran (dispersed) phase was kept while changing the concentrations of $SiO_2$ NP and PSS in the PEG (continuous) phase constant (e.g., FIG. 18). Without any NPs and/or PE in the continuous phase, the dextran/PDADMAC droplets remain perfectly spherical, and droplets undergo coalescence, indicating a lack of stabilizing membrane.

Once small amounts of either PE or NP were added to the continuous phase, the droplet morphology changed markedly owing to the formation of interfacial films. At 0.1% PE, complexation occurred predominantly in the continuous phase, as evidenced by the large number of satellite drops and dark patches along the interface. As the concentration of PSS in the continuous phase was increased to 2%, complexation occurred at the interface, resulting in wrinkles, and eventually inside the droplet, evidenced by the dark coacervate phase at 2%, consistent with previously reported results. For 2% NP present in the continuous phase, and varying PSS concentrations from 0.1 to 1%, the inner PEG drop size is decreased and eventually eliminated, ending with a single-phase, wrinkled microcapsule. By further increasing the concentration of $SiO_2$ NP in the continuous phase, a similar trend is observed; the inner PEG drop size is reduced and then eliminated. At high concentrations of PSS, the polyelectrolyte structure ultimately dominates; complexation, likely between the two PEs, occurs within the dextran/PDADMAC droplets, regardless of NP concentration. These results suggest including both anionic species during fabrication enables finer control of the accessible structures.

Figures 19A, 19B:
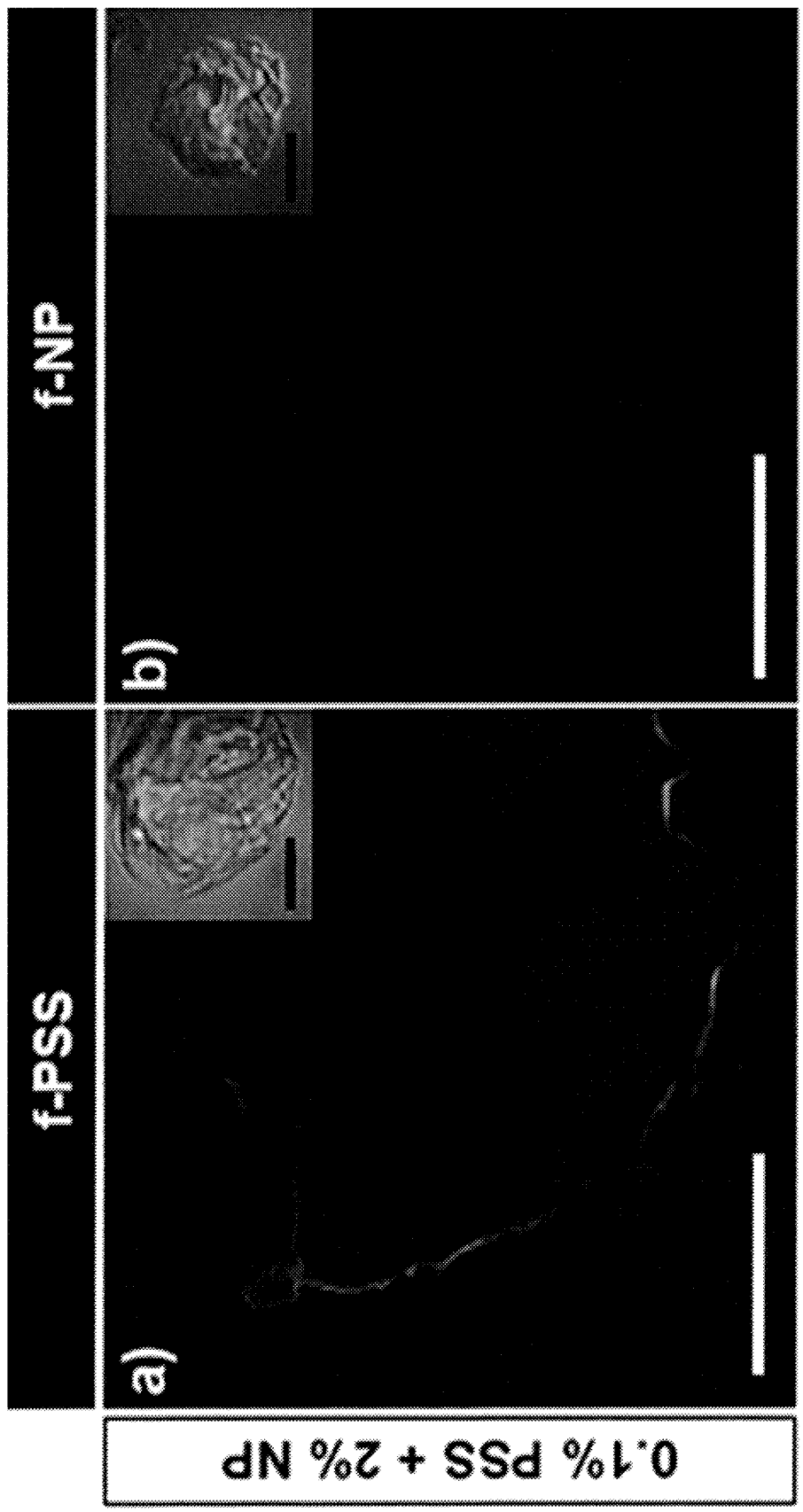
FIGS. 19A-19D are images of microcapsules having a film formed by complexation of two charged electrolytes and a charged nanoparticle.
Figures 19C, 19D:
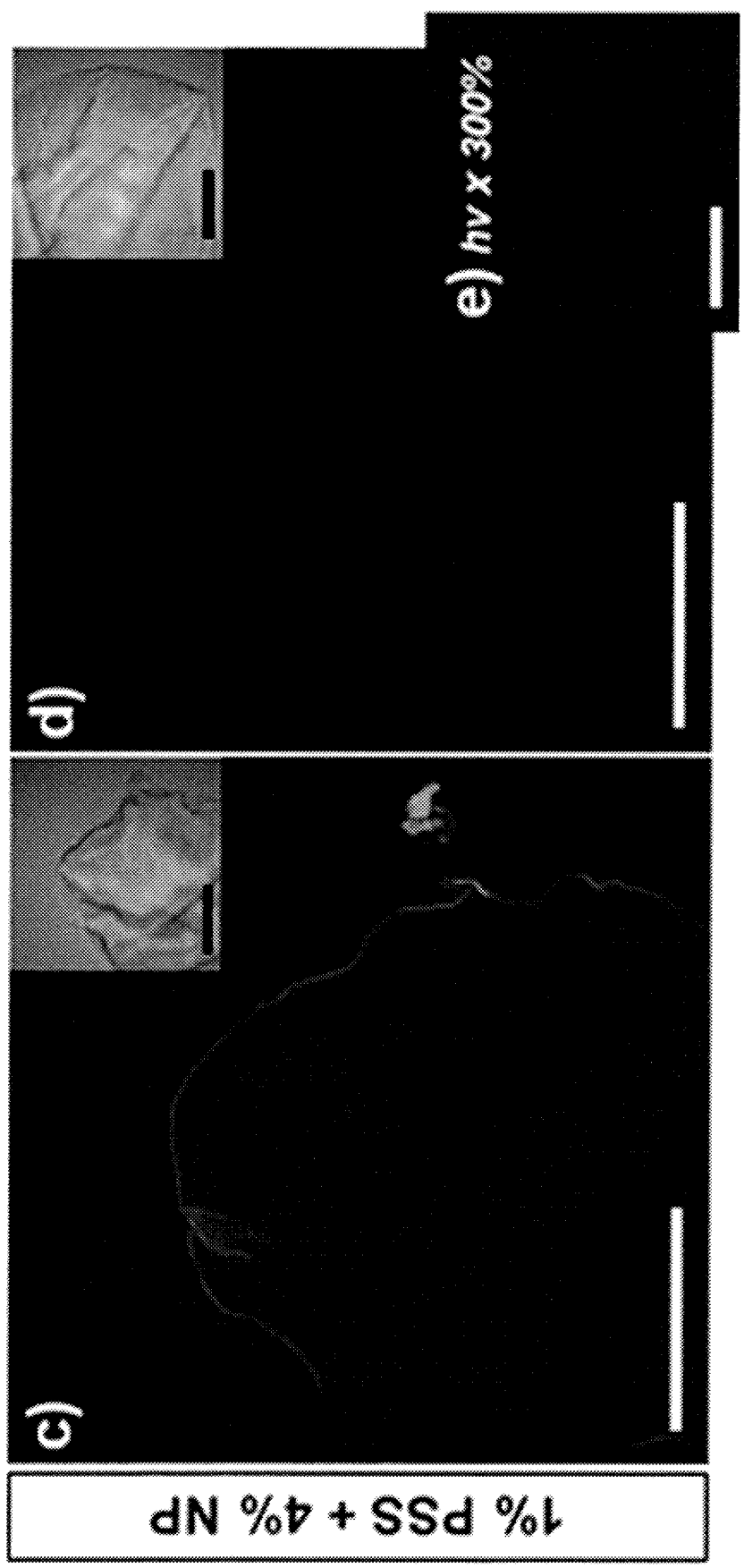

Visually, the hybrid microcapsules adopted structures that resemble both PE/PE (FIG. 18, top row) and NP/PE (FIG. 18, left column) structures; that is, at 0.1% PSS, double emulsions are still observed (similar to NP/PE microcapsules) and at 1% PSS, the microcapsules are single-phase and wrinkly (similar to PE/PE microcapsules). To discern which species make up the shells/films, and to test whether both PE and NP are incorporated, fluorescently tagged PSS (f-PSS) or fluorescent core-shell/film $SiO_2$ NP (f-NP) were added to the continuous phase and imaged with confocal microscopy. With 0.1% PSS and 2% NP in the continuous phase, both PE and NP are present in the shell/film, as shown in FIGS. 19A-19B. Moreover, PSS is present in the microcapsule interior, but not in the internal PEG droplet, consistent with the slightly greater affinity of PSS for dextran. At higher PSS concentrations (e.g., 1 PSS, FIG. 3c-d), the shell/film is primarily composed of PSS. Substantially increasing the laser intensity suggests that there may be a small amount of NP incorporated in the shell/film at such a high PE concentration, e.g., as seen in FIG. 19D. These observations suggest that the anionic species, PSS and the NP, compete to complex with the cationic PE, PDADMAC. The presence of NP in the continuous phase promotes interfacial complexation, as it reduces the flux of PDADMAC out of the dextran drop by complimenting it at the interface. As PSS concentration was increased, the structure was increasingly dominated by the PSS flux and complexation with the PDADMAC. Including both species enables tuning of the microcapsule formation by exploiting both mechanisms. By tuning PSS and NP concentrations in the continuous phase, it is possible to vary the size of the internal droplets and tune the relative makeup of the shell/film.

Figure 20G:
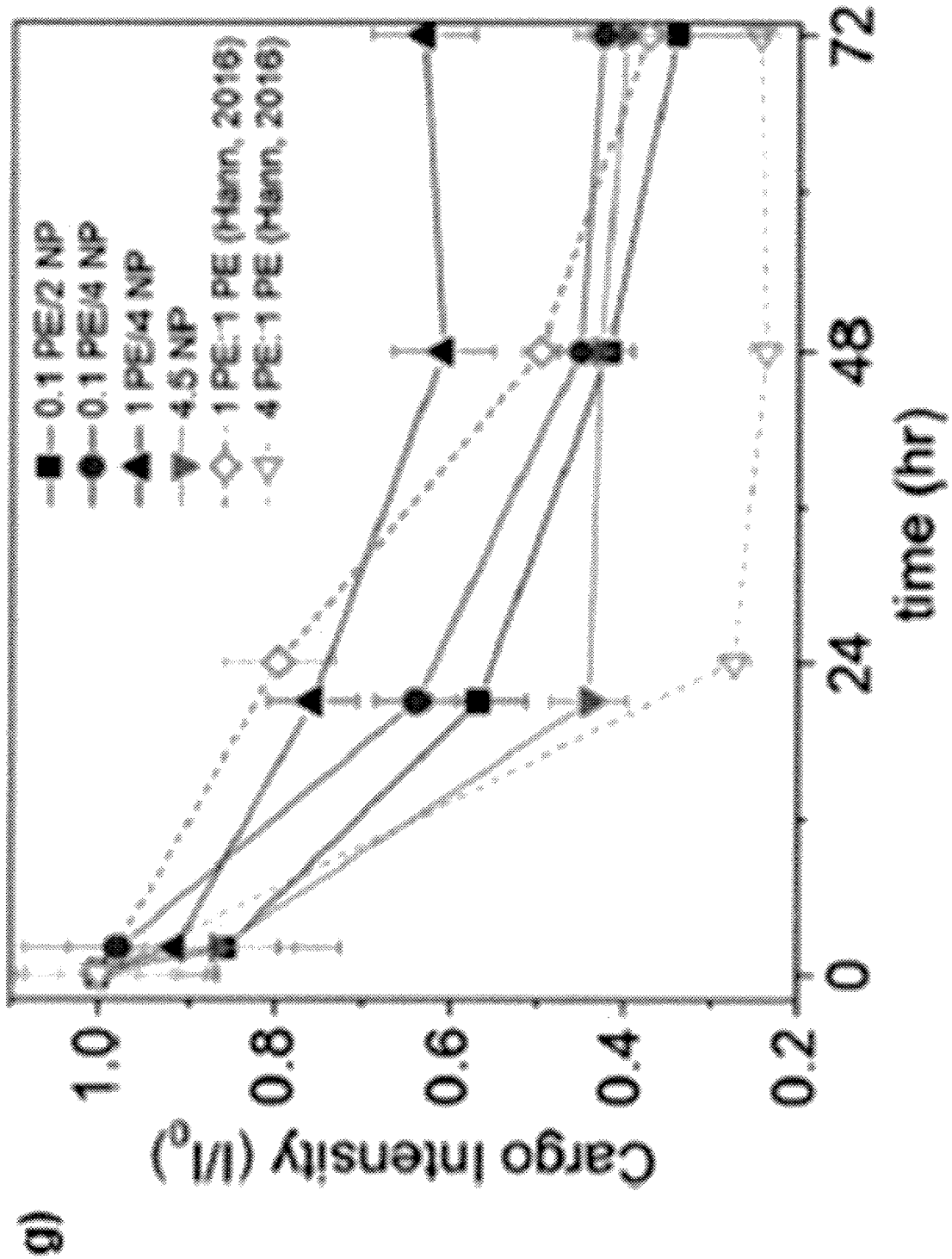
FIG. 20G is a graph of the microcapsules under osmotic stress.

The ability to tune the makeup of the shell/film by changing the concentrations of PE and NP in the continuous phase potentially enables the control of the mechanical properties of the shell/film. The PE/PE microcapsules are easily reinflated without losing the shell/film integrity when subjected to pure water (negative osmotic stress) (FIG. 20A). The NP/PE microcapsules, in contrast, rupture when exposed to pure water likely due to the brittleness of the shell/film made of a high concentration of nanoparticles (FIG. 20B). By incorporating a small amount of PE in the microcapsule shell/film, the robustness of the shell/film is dramatically improved against osmotic stress. The microcapsules are reinflated, similar to PE/PE microcapsules, indicating that they are likely softer and more flexible (FIG. 20C-20E). For comparison, when a shell/film is not initially made (e.g. 2% PSS), undergoing microdialysis results in a loose coacervate (FIG. 20F).

The integrity of the shell/film under osmotic stress was further probed by monitoring the retention of an encapsulated macromolecule. Microcapsules are prepared by electrospraying fluorescent dextran (MW=70 k)/0.5% PDADMAC droplets into the PEG phase with 2 or 4% NP and 0.1 or 1% PSS. Hybrid microcapsules are subsequently subjected to osmotic stress by exposing them to DI water. The evolution of the intensity of the encapsulated fluorescent dextran is monitored for each population; a loss in relative intensity indicates release of the encapsulated dextran. While the relatively robust PE/PE microcapsules slowly release dextran under osmotic stress, NP/PE microcapsules lose close to 60% of dextran within the first 24 hours. The remaining 40% of the dextran appears to be incorporated into the shell/film, as the shell/film's intensity remains approximately constant after 24 h. The anionic PE PSS is incorporated into the shell/film to form hybrid capsules. Release profiles from these hybrid microcapsules resemble the profiles obtained for PE/PE microcapsules. After 24 h, there is a distribution from the 4.5% NP/PE to the 1:1 PE/PE capsules, in which 0.1% PSS hybrid capsules have released about 40% dextran, while 1% PSS hybrid capsules have released only 20%, similar to the PE/PE microcapsules. Interestingly, the 1% PE+4% NP/PE hybrid microcapsules have a slower release profile than that of the other capsules. After longer times, these capsules may ultimately release the dextran. These observations again clearly suggest that the mechanical robustness of microcapsules against osmotic stress can be tuned and enhanced by varying the concentration of PE and NP in the continuous phase during electrospraying.

Figure 21:
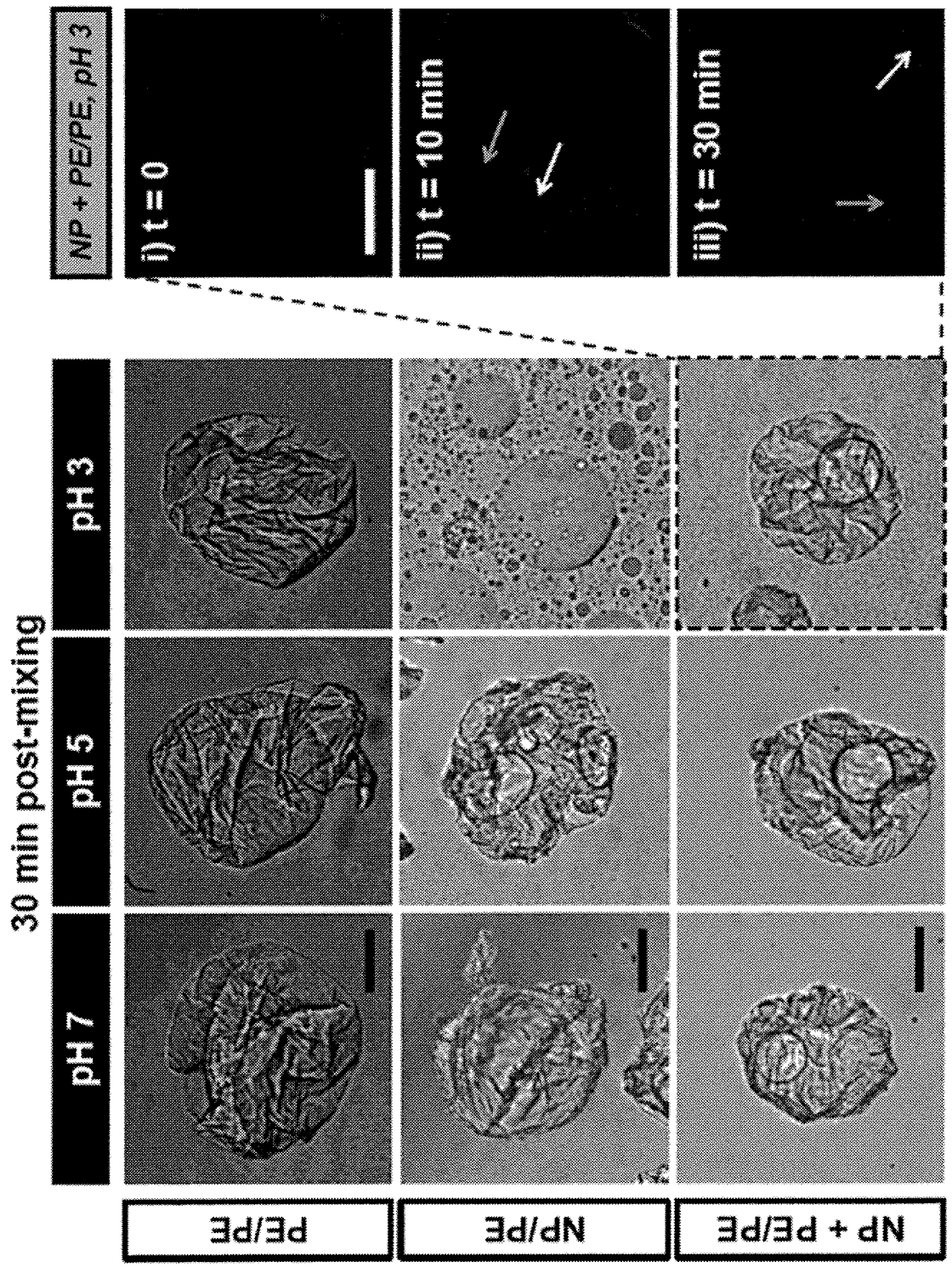
FIG. 21 is an image of microcapsules having a film formed by complexation a first and second type of charged electrolytes, nanoparticles and charged electrolytes, and two types of charged electrolytes and nanoparticles.

The PE/PE and NP/PE microcapsules disassemble under high salt and low pH conditions, respectively. By including both anionic species in the hybrid microcapsules, the stimuli-responsive properties can also be tailored. PE/PE microcapsules do not respond to changes in the solution pH as they are made of two strong PEs which have permanent charges along the backbone. In contrast, NP/PE microcapsules disassemble upon exposure to a low pH (pH 3) likely due to $SiO_2$ NPs losing their anionic charge, and thus their ability to maintain association with PDADMAC. Even with a small amount of anionic PE included in the 0.1% PE+2% NP/PE microcapsule, the disassembly of the microcapsule is suppressed while the internal droplets are maintained over at least 30 min, e.g., FIG. 21. Interestingly, confocal microscopy of NP+PE/PE microcapsules indicates that some NP are liberated from the shell/film (green arrows) during pH drop; however complexation between the two PEs is apparently sufficient to maintain the shell/film structure and keep some NPs incorporated in the shell/film (white arrows). This ability to tune the stimuli-responsive properties can be crucial in the application of these capsules.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A process for forming microcapsules in an aqueous dispersion, comprising:

injecting (1) a dispersed phase that includes at least a first component and a first hydrophilic compound into (2) a continuous phase that includes at least a second component and a second hydrophilic compound, the first component and the second component being mutually attractive, such that a film is formed by complexation of the first component and the second component, and wherein (a) one of the first component and the second component is a nanoparticle and the other of the first component and the second component comprises a charged electrolyte or a polyelectrolyte, (b) one of the first hydrophilic compound and the second hydrophilic compound comprises polyethylene glycol (PEG), or both (a) and (b).

2. The process of claim 1, wherein at least one of the dispersed phase and the continuous phase is aqueous.

3. The process of claim 1, wherein the first component is a nanoparticle and the second component is a charged electrolyte or a polyelectrolyte.

4. The process of claim 1, wherein one of the first component and the second component is a nanoparticle, and the other of the first component and the second component is a polyelectrolyte.

5. The process of claim 1, wherein (a) one of the first hydrophilic compound and the second hydrophilic compound comprises dextran.

6. The process of claim 1, wherein the process is performed to give rise to a two-phase aqueous system.

7. The process of claim 1, wherein the process is performed to give rise to a three-phase aqueous system.

* * * * *

UNITED STATES PATENT AND TRADEMARK OFFICE
CERTIFICATE OF CORRECTION

| | | |
|---|---|---|
| PATENT NO. | : 12,330,127 B2 | Page 1 of 3 |
| APPLICATION NO. | : 17/537840 | |
| DATED | : June 17, 2025 | |
| INVENTOR(S) | : Daeyeon Lee et al. | |

It is certified that an error appears in the above-identified patent and that said Letters Patent is hereby corrected as shown below:

On the Title Page

Item (56) In Other Publications,
Under Column no. 1, Page 2, Line no. 9, Replace:
""Unlralow"
With:
--"Ultralow--

In the Specification

Under Column no. 2, Line nos. 66-67, Replace:
"invention."
With:
--invention;--

Under Column no. 3, Line no. 57, Replace:
"invention"
With:
--invention;--

Under Column no. 4, Line no. 9, Replace:
"40C"
With:
--14C--

Under Column no. 14, Line no. 55, Replace:
"FIG."
With:
--FIGS.--

Signed and Sealed this
Nineteenth Day of August, 2025

Coke Morgan Stewart
*Acting Director of the United States Patent and Trademark Office*

Under Column no. 15, Line no. 32, Replace:
"till."
With:
--$t_{fill}$.--

Under Column no. 15, Line no. 33, Replace:
"FIG."
With:
--FIGS.--

Under Column no. 16, Line no. 1, Replace:
"FIG."
With:
--FIGS.--

Under Column no. 16, Line no. 65, Replace:
"the a"
With:
--the--

Under Column no. 17, Line no. 52, Replace:
"NPsdrops"
With:
--NPs drops--

Under Column no. 18, Line no. 42, Replace:
"FIG. S3A"
With:
--FIG. 16A--

Under Column no. 18, Line no. 43, Replace:
"FIG. S3B"
With:
--FIG. 16B--

Under Column no. 19, Line no. 67, Replace:
"PSS,"
With:
--% PSS,--

Under Column no. 19, Line no. 67, Replace:
"FIG."
With:
--FIGS.--

CERTIFICATE OF CORRECTION (continued)
U.S. Pat. No. 12,330,127 B2

Under Column no. 20, Line no. 31, Replace:
"(FIG."
With:
--(FIGS.--

In the Claims

Under Column no. 22, Claim 5, Line no. 23, Replace:
"(a) one"
With:
--one--